(12) United States Patent
Munroe et al.

(10) Patent No.: US 10,046,094 B1
(45) Date of Patent: Aug. 14, 2018

(54) POLYMER COATED BIODEGRADABLE STENT MATERIAL AND METHODS OF USE

(71) Applicants: Norman Munroe, Miami, FL (US); Elnaz Mirtaheri, Miami, FL (US)

(72) Inventors: Norman Munroe, Miami, FL (US); Elnaz Mirtaheri, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 15/801,574

(22) Filed: Nov. 2, 2017

(51) Int. Cl.
*A61L 33/00* (2006.01)
*A61L 33/02* (2006.01)
*A61L 33/06* (2006.01)

(52) U.S. Cl.
CPC ......... *A61L 33/0094* (2013.01); *A61L 33/022* (2013.01); *A61L 33/068* (2013.01)

(58) Field of Classification Search
None
See application file for complete search history.

(56) References Cited

U.S. PATENT DOCUMENTS

| 2009/0081313 A1* | 3/2009 | Aghion | A61L 27/047 424/641 |
| 2016/0262915 A1* | 9/2016 | Mangiardi | A61K 31/436 |

OTHER PUBLICATIONS

Gill, Puneet Kamal S., "Assessment of Biodegradable Magnesium Alloys for Enhanced Mechanical and Biocompatible Properties" (2012). FIU Electronic Theses and Dissertations. 714. (Year: 2016).*

Bolshakov, S., Pharr, G. M., "Influences of pileup on the measurement of mechanical properties by load and depth sensing indentation techniques." Journal of Materials Research, Apr. 1998, 13 (4): abstract.

Di Mario, C. et al., "Drug-Eluting Bioabsorbable Magnesium Stent." Journal of Interventional Cardiology, Dec. 2004, 17 (6): abstract.

Erbel, R. et al "Temporary scaffolding of coronary arteries with bioabsorbable magnesium stents: a prospective, non-randomised multicentre trial." The Lancet, Jun. 2007, 369 (9576): abstract.

Erne, P. et al "The road to bioabsorbable stents: reaching clinical reality?" Cardiovasc. Intervent. Radiol., 2006, 29 (1): abstract.

Gamry Instruments, "Application Note: Basics of Electrochemical Impedance Spectroscopy." [retrieved on Nov. 16, 2017] Retrieved from the Internet: <URL: www.gamry.com/assets/Application-Notes/Basics-of-EIS.pdf>.

(Continued)

*Primary Examiner* — Carlos A Azpuru
*Assistant Examiner* — Casey S Hagopian
(74) *Attorney, Agent, or Firm* — Saliwanchik, Lloyd & Eisenschenk

(57) ABSTRACT

The invention pertains to methods of treating alloys, particularly, biodegradable alloys containing Mg, Zn or Fe. The alloys can be treated with at least one of the following procedures: mechanical polishing, anodization, and polymer coating. Advantageously, methods provided herein enhance the anti-thrombogenicity of the alloy surface. Such materials can be used for preparing biomedical devices, such as endovascular implants, vascular implants, drug-eluting stents, orthopedic prostheses, or implantable chips. Methods of treating a subject by implanting the biomedical devices into the subject are also provided.

16 Claims, 18 Drawing Sheets

(56) References Cited

OTHER PUBLICATIONS

Gill, P. et al., "Corrosion and Biocompatibility Assessment of Magnesium Alloys." Journal of Biomaterials and Nanobiotechnology, 2012, 3: 10-13.

Gill, P. et al., "Effect of Manufacturing Process on the Biocompatibility and Mechanical Properties of Ti-30Ta Alloy." J. Mater. Eng. Perform., Jul. 2011, 20 (4): 819-823.

Gill, P., Munroe, N., "In-Vitro Corrosion Studies of Bioabsorbable Alloys." Magnesium Technology, 2012, abstract.

Heublein, B. et al., "Biocorrosion of magnesium alloys: a new principle in cardiovascular implant technology?" Heart, 2003, 89: 651-656.

Kubásek, J., Vojtěch, D. "Mechanical Properties and Corrosion Behaviour of Biodegradable Magnesium Alloys." Metal, 2011, 18: 1-6.

Lango, T. et al., "Diffusion coefficients and solubility coefficients for gases in biological fluids and tissues: a review." Undersea Hyperb. Med., 1996, 34 (4): abstract.

Li, Z, "Mg/Hydroxyapatite composites for potential bio-medical applications." Thesis submitted for the degree of M. Phil at Brunel University: Brunel Centre for Advanced Solidification Technology (BCAST), Aug. 2010, i-105.

Peeters, P. et al., "Preliminary results after application of absorbable metal stents in patients with critical limb schemia." Journal of Endovascular Therapy, Feb. 2005, 12 (1): abstract.

Pound, B. G., "Corrosion behavior of nitinol in blood serum and PBS containing amino acids." Journal of Biomedical Materials Research Part B: Applied Biomaterials, Aug. 2010, 94 (2): abstract.

Sawyer, P. N. et al., "Electrochemical Aspects of Thrombogenesis—Bioelectrochemistry Old and New." Journal of the Electrochemical Society, Jul. 1974, 121 (7): 221C-234C.

Schmidt, M. Steinemann, S. G., "XPS studies of amino acids adsorbed on titanium dioxide surfaces." Fresenius' Journal of Analytical Chemistry, May 1991, 341 (5-6): abstract.

Song, G. Song, S., "A Possible Biodegradable Magnesium Implant Material." Advanced Engineering Materials, Apr. 2007, 9 (4): abstract.

Song, G., "Control of biodegradation of biocompatable magnesium alloys." Corrosion Science, Apr. 2007, 49 (4): abstract.

Song, G., Atrens, A., "Corrosion mechanisms of magnesium alloys." Advanced Engineering Materials, Sep. 1999,1 (1): abstract.

Staiger, M. P. et al., "Magnesium and its alloys as orthopedic biomaterials: A review." Biomaterials, Mar. 2006, 27 (9): abstract.

Ulery, B. D. et al., "Biomedical applications of biodegradable polymers." Journal of Polymer Science Part B: Polymer Physcis, Jun. 2011, 49 (12): abstract.

Wang, Y. et al., "In vitro degradation behavior of M1A magnesium alloy in protein-containing simulated body fluid." Materials Science and Engineering: C, Apr. 2011, 31 (3): abstract.

Witte, F. et al., "Degradable Biomaterials based on Magnesium Corrosion." Current Opinion in Solid State and Materials Science, 2008, 12 (5-6): abstract.

Witte, F. et al., "In vitro and in vivo corrosion measurements of magnesium alloys." Biomaterials, Mar. 2006, 27 (7): abstract.

Witte, F. et al., "Magnesium-hydroxyapatite Composites: A Novel Approach to Biodegradable Metals." Biomaterials, 2007, 8: 2163-2174.

Ye, X. et al., "In vitro corrosion resistance and cytocompatibility of nano-hydroxyapatite reinforced Mg—Zn—Zr composites." Journal of Materials Science: Materials in Medicine, Apr. 2010, 21 (4): abstract.

Zberg, B. et al. "MgZnCa glasses without clinically observable hydrogen evolution for biodegradable implants." Nature Materials, Sep. 2009, 1-5, DOI: 10.1038/NMAT2542.

\* cited by examiner

POLYMER COATED BIODEGRADABLE STENT MATERIAL AND METHODS OF USE

BACKGROUND OF INVENTION

The coronary stent market was reported to be $8.8 billion in 2015 and is expected to grow. An increase in cardiovascular disorders is a primary reason for increasing demand for coronary stents.

Various types of stents are currently available; including bare-metal stents (BMS), bio-absorbable stents, coated stents, drug-eluting stents (DES), and dual-therapy stents. BMS have been observed to cause late-stent thrombosis (blood clots) and in-stent restenosis, which can lead to long-term endothelial dysfunction and/or a chronic inflammation. In-stent restenosis occurs between 3 to 6 months after implantation, whereas late-stent thrombosis occurs between 1 and 12 months after implantation. Although the rate of restenosis decreased initially with DES, once the drug is eluted, similar problems associated with BMS may still occur.

Specifically, the formation of blood clots on a stent's surface in the coronary artery can block or obstruct blood flow, as well as cause serious complications if the clots move to a crucial part of the circulatory system, such as brain or lungs.

The use of biodegradable polymeric stents has the advantage of reducing late stent thrombosis, secondary surgeries, and medical cost for post-percutaneous coronary intervention (PCI) therapy. Polymer stents, however, lack the mechanical properties similar to their permanent metallic counterparts and may lead to increased inflammatory response, neointimal proliferation, and/or extensive cell infiltration.

When in contact with vascular blood flow, the alloys currently used in biocompatible implants are prone to formation of thrombi. The composition of the bulk materials (e.g., alloys) and their surface treatment directly affect surface characteristics responsible for the biocompatibility of the implant or device that employs such materials. These surface characteristics can be, for example, surface composition, roughness, wettability, surface free energy (SFE), and surface morphology.

Specifically, according to Sawyer et al. thrombosis is initiated by an electron transfer process between the surface of a biomaterial and fibrinogen in the blood, leading to a clotting cascade at anodic sites. In the case of cardiovascular stents, thrombogenicity can depend on the stent material's intrinsic properties such as, for example, corrosion resistance, hemocompatibility, and mechanical integrity. Furthermore, extrinsic properties of a stent, such as dimensions, drug and/or polymer coatings, placement with respect to the vessel wall, which imposes specific flow disruptions (e.g., stagnation and recirculation), can also affect the stent's thrombogenicity.

Antithrombogenic properties, or properties responsible for inhibiting the formation of thrombus, are therefore desirable for implants placed in contact with vascular blood before a proper endothelial layer can form at the surface of the stents. Absent any antithrombogenic treatment, deposition of platelets and subsequent formation of thrombus due to exposure to various blood proteins such as fibrinogen, fibronectin, vitronectin, immunoglobulin, and von Willebrand factor (vWF) will quickly ensue.

As a result, it remains a challenge to design a biocompatible and hemocompatible material capable of enhancing the anti-thrombogenicity of stents while retaining advantageous properties of metallic stents.

BRIEF SUMMARY

The subject invention provides methods of treating alloys. Alloys treated according to the methods of the invention are particularly useful in biomedical applications.

In preferred embodiments, the alloys are biodegradable, such as magnesium-based alloys, preferably comprising zinc and calcium as minor components, or iron-based alloys, such as stainless steel. In specific embodiments, the biodegradable alloys can be treated by one or more of the following procedures: mechanical polishing (MP), anodization (A), and polymer coating (P). In preferred embodiments, alloys are treated by all of the three procedures.

Advantageously, methods of the subject invention can enhance the anti-thrombogenicity of materials used in applications, such as endovascular and vascular implants, drug-eluting stents, orthopedic prostheses, and implantable chips for biomarker labeling. Accordingly, certain embodiments of the invention provide biocompatible devices comprising alloys treated according to the methods provided herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DISCLOSURE

Figure 1:
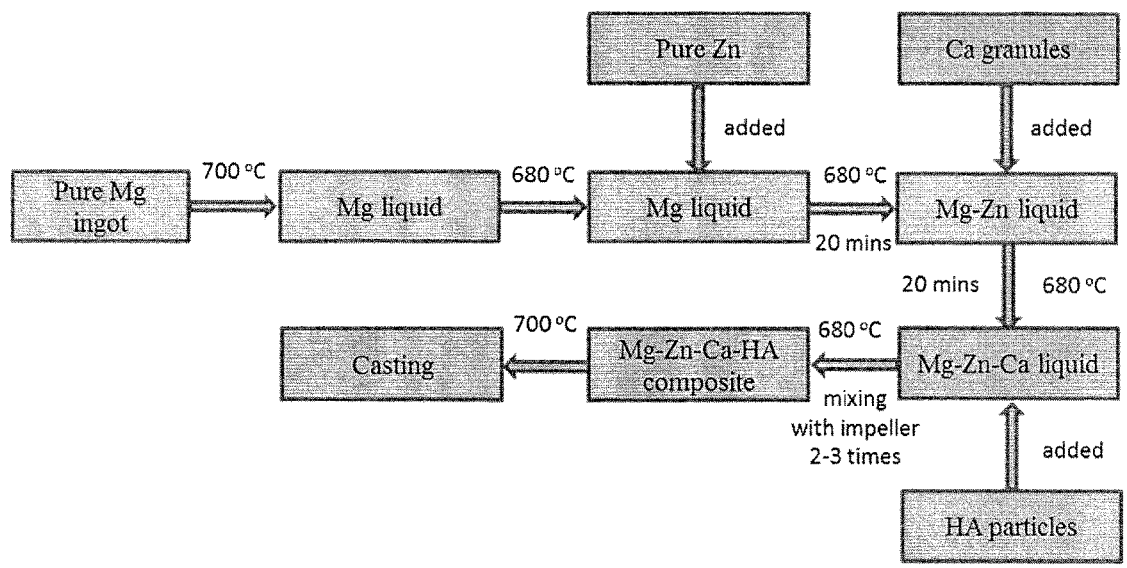
FIG. 1 is a schematic representation of the manufacturing process of alloys Mg1Zn1Ca1HA, Mg1Zn1Ca3HA, Mg5Zn1Ca, Mg5Zn1Ca1HA, and Mg5Zn1Ca3HA.

Owing to their mechanical strength, elongation properties, resistance to fatigue, and drug elution kinetics, alloys are suitable in biomedical applications, such as making implants. The subject invention provides methods of treating alloys, particularly, alloys used in various biomedical applications including, for example, implants and prostheses. The methods of the invention provide biomedical implants with superior properties, for example, reduced formations of blood clots when placed in contact with blood.

Accordingly, in some embodiments, the subject invention provides methods for treating an alloy, such as a biodegradable alloy, that improves the alloy's in-vivo interaction with the biological environment in which it is placed. In specific embodiments, the treatment comprises subjecting a surface of an alloy to one or more of the following: mechanical polishing, electrochemical treatment, and polymer coating.

In preferred embodiments, the treatment comprises subjecting a surface of an alloy to two of the following procedures: mechanical polishing, electrochemical treatment, and polymer coating. In particularly preferred embodiments, the treatment comprises subjecting a surface of an alloy to all of the following procedures: mechanical polishing, electrochemical treatment, and polymer coating.

In some embodiments, the methods provided herein can be used to modify the surface properties of biocompatible devices. In other embodiments, the methods can be used to modify the surface properties of biocompatible devices comprised of alloys, particularly, biodegradable alloys such as Mg, Zn or Fe containing alloys.

In some embodiments, the methods provided herein can be used to modify the surface properties of biomedical devices comprised of alloys used in cardiovascular applications. Such implants come in contact with blood and/or blood vessels. Non-limiting examples of biomedical devices used in cardiovascular applications include cardiovascular implants, endovascular implants, and drug-eluting stents.

In addition, alloys provided herein can be applied in implantable chips for biomarker labeling as well as for orthopedic prostheses.

Examples of biodegradable alloys are magnesium-based alloys and iron-based alloys (e.g., stainless steel). In some embodiments, the biodegradable alloys provided herein are magnesium-based alloys comprising, in addition to Mg, at least one of the following components: zinc (Zn), calcium (Ca), gadolinium (Gd), and hydroxyapatite (HA).

In preferred embodiments the biodegradable alloys comprise Mg as the major component and Zn and Ca as minor components. In an exemplary embodiment, the magnesium alloy comprises 98% Mg, 1% Zn, and 1% Ca. This composition is designated as "Mg1Zn1Ca" or "MZC", the two names being used interchangably hereafter. In some embodiments, a biodegradable alloy in accordance with the subject invention consists of a magnesium-based alloy such as MZC; alternatively, it can further comprise one or more alloys different from a magnesium-based alloy.

Advantageously, Mg-based alloys further comprising Zn and Ca have microstructures consisting of segregated phases in the grain boundaries. These phases include, for example, α-Mg solid solution, and binary and ternary intermetallics (e.g., $Mg_2Ca$, $CaZn_2$, $MgZn_2$, $CaZn_5$, $Ca_2Mg_6Zn_3$, and/or $Ca_5(PO_4)_3(OH)$), all of which contribute to improved strength, hardness, and/or corrosion resistance of the alloys.

Mechanical polishing (denoted as "MP") is the smoothing of a surface using mechanical tools and abrasives. Mechanical polishing can be performed using abrasives such as silicon carbide paper, diamond based abrasive, and cubic boron nitride.

Depending upon the desired surface roughness, abrasives with different grit/particle sizes can be employed during mechanical polishing. In some embodiments, multiple grit/particle sizes can be chosen to polish an alloy.

The grit level of the abrasive can be varied to provide mechanical polishing of varying degrees. In preferred embodiments, abrasives having standard American National Standards Institute (ANSI) grit from 60 to 1200, for example, 60, 80, 120, 180, 240, 320, 400, 600, 800, and 1200 are used. In particularly preferred embodiments, abrasives are used having standard ANSI grit from 400 to 800, and particularly, about 600.

In certain embodiments, to prevent the hydrolysis of the alloys, the usage of water-based solutions is avoided during mechanical polishing. When water-based solutions are not used, organic solvents or a mixture of organic solvents are used as cooling agent. Examples of such organic solvents include ethanol, ethylene glycol, perchloric acid, and methanol. In preferred embodiments, ethanol-ethylene glycol (3:1) was used as cooling agent.

In preferred embodiments, the alloys surface is mechanically polished to produce surface roughness from 0.02 µm to 1.0 µm, preferably, from 0.03 µm to 0.09 µm, more preferably, from 0.04 µm to 0.08 µm, even more preferably, from 0.05 µm to 0.07 µm, or about 0.06 µm. In specific embodiments, the alloys surface is mechanically polished to produce surface roughness of 0.040 µm, 0.041 µm, 0.042 µm, 0.043 µm, 0.044 µm, 0.045 µm, 0.046 µm, 0.047 µm, 0.048 µm, 0.049 µm, 0.050 µm, 0.051 µm, 0.052 µm, 0.053 µm, 0.054 µm, 0.055 µm, 0.56 µm, 0.057 µm, 0.058 µm, 0.059 µm, 0.060 µm, 0.061 µm, 0.062 µm, 0.063 µm, 0.064 µm, 0.065 µm, 0.66 µm, 0.067 µm, 0.058 µm, 0.069 µm, or 0.070 µm.

Specific details of the parameters of mechanical polishing of metal surfaces, particularly, alloys surfaces, and more particularly, Mg or Fe alloys surfaces, to achieve a target roughness are well known to a skilled artisan and such embodiments are within the purview of the invention.

In certain embodiments, the alloy surfaces are electrochemically treated to increase the thickness of the native oxide layer at the surface of the alloy to produce a protective layer on the surface. In preferred embodiments, the treatment requires the surface of the alloy to serve as the anode of a circuit, a process known as "anodization" (denoted as "A"). In exemplary embodiments, anodization of a Mg-based alloy is conducted using various electrolytes and voltages to achieve a desired oxide thickness and morphology. Advantageously, anodization increases an alloy's resistance to corrosion and wear, improving the chemical and mechanical properties at its surface.

Anodizing is an electrochemical process that produced a passive oxide layer on the surface of a metal or an alloy. Anodization can be conducted using a DC-voltage source and a two-electrode configuration in an appropriate electrolyte. During the anodization process, the treated surface forms the anode electrode of an electrical circuit.

Anodization can be performed by methods known in the art. For example, a mixture of salts and electrolytes, including sodium dichromate, can be used in a low voltage, for example, less than 100 volts, can be used. Higher voltage of more than 300 volts can be used, which produces thicker coatings but higher porosity. The size and number of pores in the anodized layer depends on the alloy, electrolyte composition, and applied voltage. Anodization procedures that provide thicker coatings with reduced porosity are preferred.

In certain embodiments, stainless steel (316L) was used as the cathode during anodization during which a sweeping potential of 5 V/s was employed to a final voltage of 20 V, which was subsequently held at that level for 3000 seconds at room temperature. The applied voltage of 20 V yielded the most desirable corrosion resistance to magnesium containing alloys, particularly, MZC (Appendix III). In certain embodiments, electrolyte consisted of ethanol (nominally water-free, Sigma-Aldrich) mixed with ammonium nitrate (0.01 M).

The oxide layer ultimately affects the biocompatibility of an alloy, such as MZC, because it serves as a barrier between the bulk of the material and the electrolyte. However, this protective layer can eventually break down, enabling gradual dissolution of the implant and polymer coating.

In some embodiments, the alloy surfaces are coated with a biodegradable polymer. In preferred embodiments, the alloy surfaces are first anodized and then coated with a biodegradable polymer.

Non-limiting examples of biodegradable polymers that can be used as a surface coating include poly(α-esters), polyglycolides, polylactides, poly(lactide-co-glycolide), polyhydroxyalkanoates, polycaprolactone, poly(propylene fumarate), polyanhydrides, polyacetals, poly (ortho esters), polycarbonates, polyurethanes, polyphosphazenes, polyphosphoesters, poly(ester ether)s, or poly(amide ester)s. Non-limiting examples of biodegradable polymers suitable for use in the methods of the invention are described in the Ulery et al. reference (Ulery et al. (2011) *J Polym Sci B Polym Phys.;* 49(12): 832-864), which is herein incorporated by reference in its entirety.

In preferred embodiments, the biodegradable polymers are copolymers comprising poly(glycolic acid) (polyglycolide) such as poly(glycolic acid-co-caprolactone) (PGCL), poly(glycolic acid-co-trimethylene carbonate), polylactic-co-glycolic acid), or a combination thereof. Additional biodegradable polymers are known in the art and such embodiments are within the purview of the invention.

In an exemplary embodiment, an alloy is coated with a PGCL copolymer by dipping the alloy sample in a solution of PGCL. The rate of dipping and subsequent withdrawal of the alloy in the polymer solution can be modified by a person skilled in the art to control the thickness and uniformity of the polymer coating.

Figure 22:
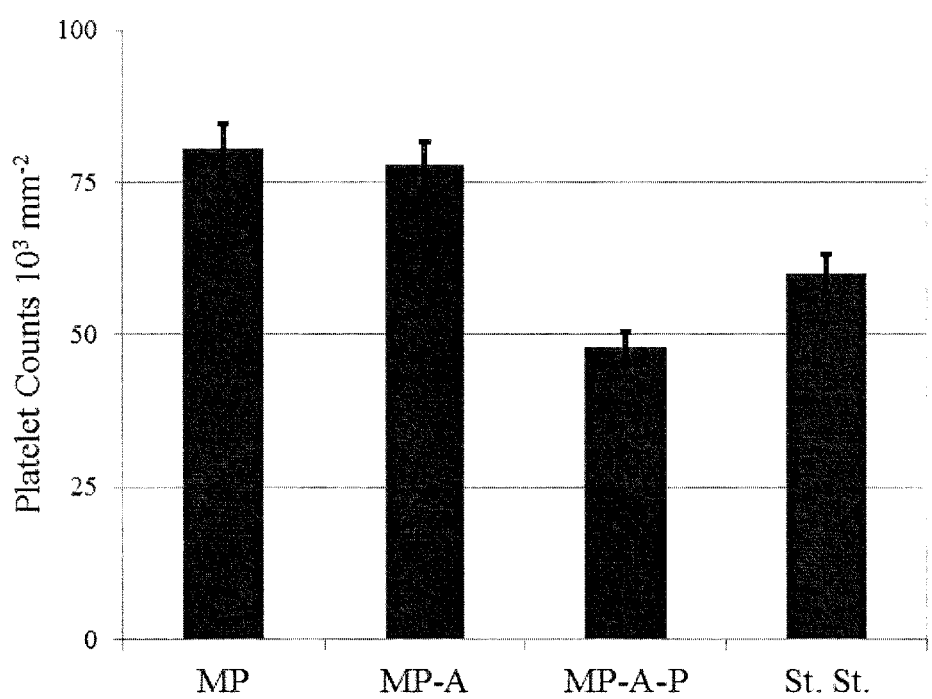
FIG. 22 shows the results of platelet adherence on MZC's surfaces after surface treatments (MP-A-P, i.e., mechanically polished, anodized, and polymer-coated) in comparison to as-cast (MP) or anodized-only MZC (MP-A) and stainless steel (S.S.).

The alloys' surfaces, particularly, Mg alloys' surfaces, treated according to the methods of the invention exhibit antithrombogenic characteristics and enhanced corrosion resistance. In exemplary embodiments, in-vitro thrombogenicity tests revealed low platelet adherence to anodized and polymer-coated ("A-P") MZC as compared with as-cast and mechanically polished, mechanically polished and anodized MZC, and stainless steel SS316 which was used as a control sample (FIG. 22).

Advantageously, metallic stents treated with methods provided herein results in a reduction of thrombosis and the need for additional antithrombogenic therapy, which together can greatly reduce the costs associated with post-stent treatments and provide improved disease prognosis. As such, the methods of the invention can provide biomedical devices having reduced thrombogenicity. Implants having reduced thrombogenicity reduce the need for secondary surgeries and therapies (e.g., post-percutaneous coronary intervention therapy), and lower the risk of blood clots, for example, during late-stent thrombosis and/or restenosis.

Accordingly, certain embodiments of the invention provide a device comprising an alloy, particularly, a biodegradable alloy, wherein the surface of the device is treated according to one or more of the following procedures: mechanical polishing, electrochemical treatment, and polymer coating. In preferred embodiments, the surface of the device is treated according to two of the following procedures: mechanical polishing, electrochemical treatment, and polymer coating. In particularly preferred embodiments, the surface of the device is treated according to all of the following procedures: mechanical polishing, electrochemical treatment, and polymer coating.

Various details of the processes of mechanical polishing, electrochemical treatment, and polymer coating discussed above in connection with the methods of the invention are also applicable to the devices of the invention and such embodiments are within the purview of the invention.

In preferred embodiments, the devices comprising an alloy are biomedical devices. In particularly embodiments, the biomedical devices are made from alloys, particularly biodegradable alloys, such as Mg-based, Zn-based or Fe-based alloys. In specific embodiments, the biomedical devices are made from stainless steel, Mg1Zn, Mg1Zn1Ca, Mg1Zn1Ca8Gd, Mg1Zn1Ca1HA, Mg1Zn1Ca3HA, Mg5Zn1Ca, Mg5Zn1Ca1HA, or Mg5Zn1Ca3HA.

The biomedical devices of the invention can be implanted in a patient in need thereof. Such implantation provides advantageous and superior therapy outcomes. Accordingly, further embodiments of the invention provide methods of treating a subject by implanting the biomedical devices described herein into the subject. The specific diseases to be treated, appropriate biomedical devices to be used, and appropriate methods of implanting the biomedical devices can be determined by a competent medical professional and such embodiments are within the purview of the invention.

TABLE 1

Lubricants and abrasives used during sample preparation

| Surface | Lubricant | Abrasive |
|---|---|---|
| Carbimet ® | Ethanol | SiC, 400 grit |
| Texmet ® | Ethanol-Ethylene Glycol (3:1) | Metadi ® Paste, 9 μm |
| Texmet ® | Ethanol-Ethylene Glycol (3:1) | Metadi ® Paste, 3 μm |
| Chemomet ® | Ethanol | Masterpolish ®, 0.05 μm |

MZC samples measuring approximately 1 cm×1 cm and 2 mm in thickness were mechanically polished using silicon carbide papers of grit 600. The usage of water-based solutions was avoided during polishing in order to prevent the hydrolysis of the alloy. A mixture of ethanol-ethylene glycol (3:1) was used as a cooling agent. The described procedure yielded the most desirable surface roughness among different polishing procedures.

TABLE 2

Nominal and analyzed compositions of the materials in weight percentage (wt %)

| | Nominal Composition (%) | | | | | | Analyzed Composition (%) | | | | |
|---|---|---|---|---|---|---|---|---|---|---|---|
| | Mg | Zn | Ca | HA | Gd | O | Mg | Zn | Ca | HA | Gd | O |
| Mg1Zn | Balance | 1 | NA | NA | NA | NA | Balance | 0.71 | NA | NA | NA | 12.59 |
| Mg1Zn1Ca8Gd | Balance | 1 | 1 | NA | 8 | NA | Balance | 1.01 | 0.76 | NA | 5.08 | 0.81 |
| Mg1Zn1Ca | Balance | 1 | 1 | NA | NA | NA | Balance | 1.62 | 0.37 | NA | NA | 2.28 |
| Mg1Zn1Ca1HA | Balance | 1 | 1 | 1 | NA | NA | Balance | 1.80 | 1.38 | No Analysis | NA | 4.88 |
| Mg1Zn1Ca3HA | Balance | 1 | 1 | 3 | NA | NA | Balance | 1.38 | 1.53 | No Analysis | NA | 1.93 |
| Mg5Zn1Ca | Balance | 5 | 1 | NA | NA | NA | Balance | 1.77 | 0.99 | NA | NA | 2.26 |
| Mg5Zn1Ca1HA | Balance | 5 | 1 | 1 | NA | NA | Balance | 5.03 | 1.09 | No Analysis | NA | 1.81 |
| Mg5Zn1Ca3HA | Balance | 5 | 1 | 3 | NA | NA | Balance | 5.17 | 1.04 | No Analysis | NA | 2.18 |

Materials and Methods

Alloy Manufacturing

Magnesium-based alloys, such as Mg1Zn, Mg1Zn1Ca (MZC), Mg1Zn1Ca8Gd were manufactured by melting these elements at 1000° C. under an inert atmosphere (e.g., argon) and casting in a water-cooled copper mold. The ramp-up time from room temperature to melting temperature was 1 minute and the alloys were further heat-treated at 350° C. and then water-quenched.

Another group of alloys, Mg1Zn1Ca1HA, Mg1Zn1Ca3HA, Mg5Zn1Ca, Mg5Zn1Ca1HA, and Mg5Zn1Ca3HA were manufactured in an electrical resistance furnace under an inert atmosphere (99.6% N2+0.4% SF6). The mixing process was conducted three times at 20-minute intervals with a mixing duration of 3 to 4 minutes. FIG. 1 shows the schematic for the alloy preparation and Table 2 shows the nominal and analyzed compositions of the materials in wt %.

Sample Preparation and Mechanical Polishing

Ingots were cut into samples measuring approximately 0.414 in×0.414 in×0.08 in using a linear precision saw (ISOMET 4000). Each ingot was mounted into epoxy resin with an exposed working area of approximately 0.414 in×0.414 in, which was then mechanically polished to achieve a roughness close to 0.05 microns using abrasives, abrasive papers (Buehler) and lubricants (Sigma-Aldrich). Samples were polished in four steps as shown in Table 1 below. The usage of water-based solutions was avoided during sample preparation to prevent hydrolysis of the alloy.

Anodization

Anodization is an electrochemical process that produces a passive oxide layer on the surface of an alloy such as MZC. It is conducted using a dc-voltage source and a two-electrode configuration (a cylindrical stainless steel 316L was used as the cathode) by sweeping the potential at 5 V/s to a final voltage of ~20 V and subsequently holding the voltage at that level for 3000 seconds at room temperature. The electrolyte comprised of ethanol (nominally water-free, Sigma-Aldrich) mixed with ammonium nitrate (0.01 M).

Anodization of MZC affected the nature, degree of compaction, and microstructure of its passivating surface oxide, which are characteristics that depend on parameters such as duration of the process, voltage level, and type of electrolyte used in the anodization process. The oxide layer ultimately affected the biocompatibility of MZC as it served as a barrier between the bulk of the material and the electrolyte. For a biodegradable alloy, this protective layer eventually breaks down, enabling the gradual dissolution of the material.

Polymer Coating

Polymer coating can be conducted by dipping the MZC into a 10 percent (W/V) solution of polyglycolic-co-caprolactone (PGCL; PG90:CL10) co-polymer (Bezwada Biomedical LLC) in dichloromethane (DCM) at room temperature. Prior to coating, samples were pre-heated at 180° C. for 10 minutes to eliminate entrapped air and moisture from the surface. The samples were then immersed into the polymer solution for approximately 20 seconds to allow wetting of the surface and were vertically dried in a vacuum oven (10 mbar) at 37° C. for 24 hours. The dipping and withdrawal rate was controlled using a DC motor and a function generator.

The thickness and uniformity of polymer coating are crucial, especially for implants of complicated shapes. Therefore, the dipping technique was adopted as it offers a simple procedure capable of coating implants with complex shapes.

Characterization of Surface Properties

Wettability

Contact angle measurements were conducted with a Kyowa contact angle meter model DM-CE1, using the sessile drop technique. Three different solvents were employed: distilled water (highly polar), ethylene glycol (neutral), and diiodomethane (non-polar). FAMAS analysis software was used to examine the surface free energy (SFE) parameters based on the Lifshitz-Van der Waals (LW) acid-base interaction and Kitazaki-Hata theory.

Young-Dupré Equation

The Young equation describes the relationship between the surface free energy (SFE) of the liquid ($\gamma L$), the surface free energy of the solid ($\gamma S$), the interfacial free energy between solid and liquid ($\gamma SL$), and the contact angle between the probe liquid and the examined surface ($\theta$) as seen in Equation (1) below:

$$\gamma S = \gamma L \cos \theta + \gamma SL \quad (1)$$

Corrosion Test

Potentiodynamic polarization was performed at 37° C. employing a GAMRY potentiostat (G-750) to assess the corrosion behavior of surface treated samples. The electrochemical cell comprised of the MZC sample (working electrode), a carbon rod (counter electrode), and Ag/AgCl electrode (reference electrode). Electrochemical measurements were carried out in a phosphate buffered saline (PBS) solution. Each sample was immersed in the PBS solution for approximately 5 minutes to achieve a stable open circuit potential. Potentiodynamic polarization tests were carried out at the open circuit potential and scanned from −0.1 V/Eocp to +0.5 V/Eocp at a scan rate of 5 mV/s.

Platelet Adhesion

Hemocompatibility of the surface-treated samples was evaluated by flowing porcine blood (platelets) on samples using a custom-built, multi-specimen, laminar-flow chamber. Using a peristaltic pump operated at 37° C., the blood flowed at a rate of 113 cm/s, which was within the dynamic range of velocities measured in the veins of a human body's upper limbs.

Prior to testing, MZC samples were ultrasonically cleaned for 5 minutes in DI water, followed by cleaning in 70% ethanol for 5 minutes to eliminate impurities and foreign particles on the surface. The polymer-coated samples were sterilized by exposing them to UV radiation for 40 minutes, before conducting the platelet adhesion tests. Once all the samples were placed in the chambers of the flow loop (n=5 samples at a time), a PBS solution was used to prime the loop for 10 minutes.

Approximately 500 mL of freshly collected whole porcine blood was mixed with 150 ml of sodium citrate anticoagulant. 333.5 ml of 10 mM mepacrine dye solution was added for every 500 ml of whole porcine blood to fluorescently label the platelets. The blood was passed over the metallic samples in the loop for 35 minutes. Then, the samples were washed with PBS three times to remove any residual blood components. Platelets adhered on the MZC samples were observed under a fluorescent microscope (Nikon Eclipse E 200, Nikon, Melville, N.Y.). The number of platelets adhered to each sample was counted using an image analysis software (Image J, NIH, Bethesda, Md.).

Statistical Analysis

A statistical analysis was performed on platelet adhesion data using a one-way ANOVA analysis, followed by post-hoc testing (Tukey HSD). A significant difference between materials was interpreted to occur at $p<0.05$.

Definitions:

As used herein, the singular forms "a", "an" and "the" are intended to include the plural forms as well, unless the context clearly indicates otherwise. Further, to the extent that the Willis "including", "includes", "having", "has", "with", or variants thereof are used in either the detailed description and/or the claims, such terms are intended to be inclusive in a manner similar to the term "comprising."

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. Where particular values are described in the application and claims, unless otherwise stated the term "about" meaning within an acceptable error range for the particular value should be assumed. In the context of compositions containing amounts of ingredients where the term "about" is used, these compositions contain the stated amount of the ingredient with a variation (error range) of 0-10% around the value (X±10%). Where the term "about" is used to describe target durations of time used in certain processes, the target durations of time can be varied within a range 0-10% around the target value (X±10%).

In the present disclosure, ranges are stated in shorthand, to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, and 0.7-1.0.

When ranges are used herein, combinations and sub-combinations of ranges (e.g., subranges within the disclosed range), specific embodiments therein are intended to be explicitly included.

As used herein, the term "biodegradable" refers to materials that is safely degraded or safely metabolized within a live animal, particularly, a mammal, and more particularly, a human. Therefore, a biodegradable alloy can contain a toxic metal at concentrations that do not produce toxic effects in a live animal.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Potentiodynamic Polarization Test

Figure 2:
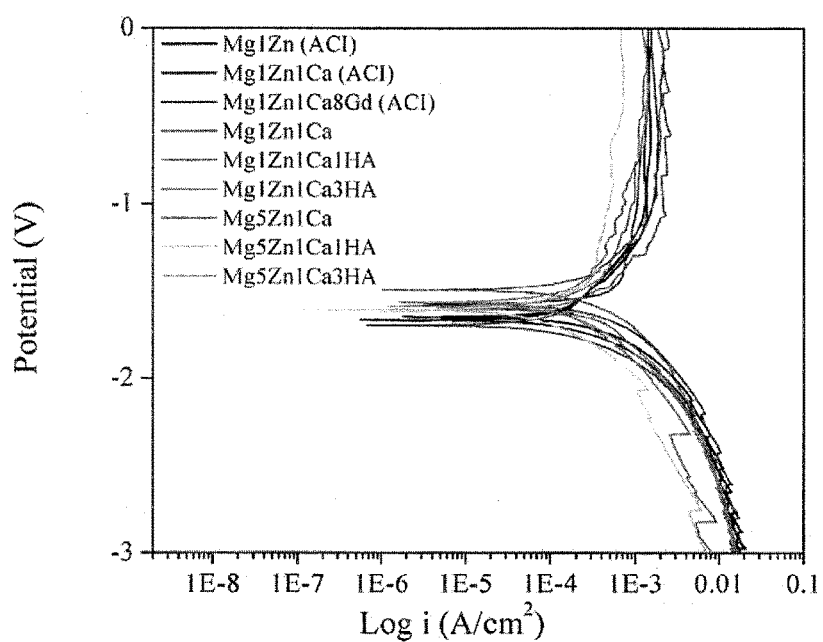
FIG. 2 shows typical potentiodynamic polarization curves of mechanically polished Mg-based alloy samples in PBS at 37° C.

FIG. 2 shows typical potentiodynamic polarization curves for mechanically polished samples. A Tafel fit was employed to analyze the polarization curves, where passivation control occurred between 0.001-0.02 A/cm² and corrosion potential ranged between −1.2 to −1.7. The jagged anodic curves were indicative of continuous breakdown (pitting corrosion) and passivation (Gill P, Munroe N. In-vitro corrosion studies of bioabsorbable alloys. Magnesium Technology, TMS, 2012; Gill P, Munroe N, Dua R, Ramaswamy S. Corrosion and Biocompatibility Assessment of Magnesium Alloys. Journal of Biomaterials and Nanobiotechnology, 2012; 3:10-13). The addition of alloying elements zinc, calcium, hydroxyapatite (HA), and gadolinium exhibited improved corrosion resistance and influenced the quantity and distribution of the binary and ternary phases. These phases have been reported to enhance the corrosion resistance properties of the alloys. The corrosion parameters of the alloys in PBS are shown in Table 3.

Figure 3:
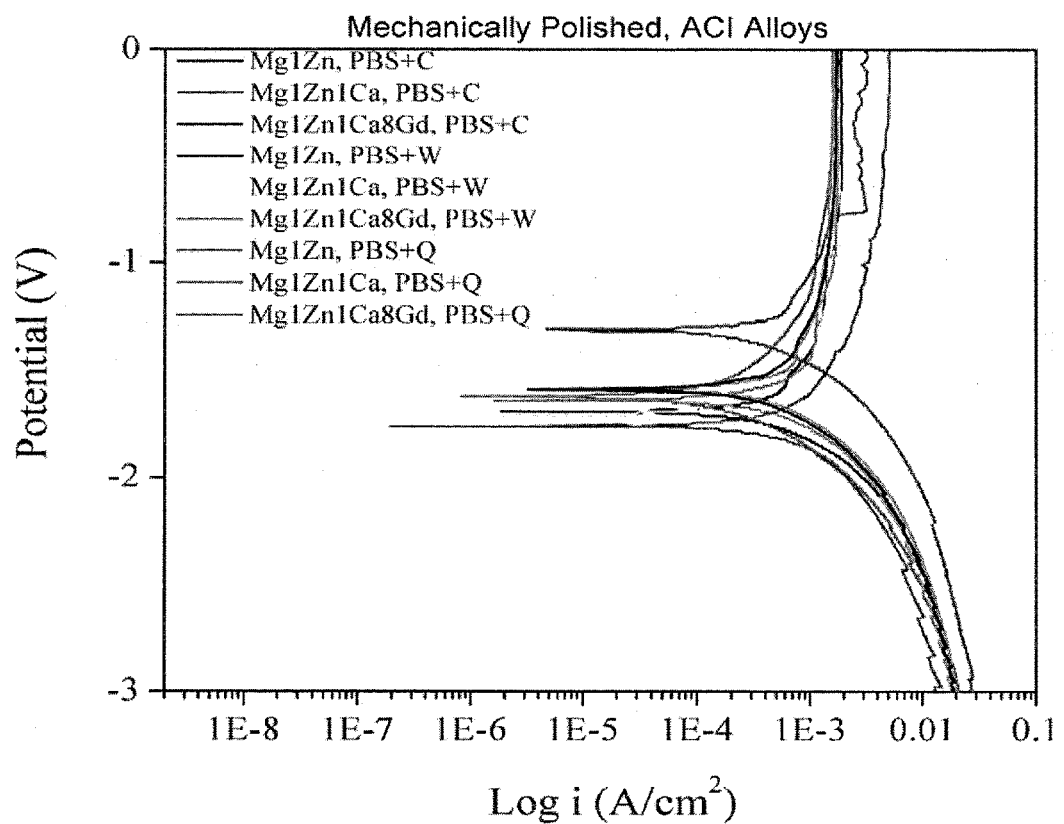
FIG. 3 shows typical potentiodynamic polarization curves of mechanically polished Mg-based alloys in PBS containing amino acids at 37° C.

The effect of amino acids on degradation behavior of Mg alloys was also studied at 37° C. by employing concentrations of amino acids typically found in human blood (C=0.25 mM; Q=0.568 mM and W=0.042 mM). The corrosion parameters of the samples in PBS and PBS with amino acids are shown in Table 4 (polarization curves, FIG. 3). Mg1Zn and Mg1Zn1Ca had the lowest corrosion rates in PBS (2.4 and 2.9 mm/year respectively); however, Mg1Zn exhibited the highest corrosion rate in PBS+W (130.11 mm/year). A similar trend was observed with the remainder of the alloys, where the corrosion rate increased in PBS with amino acids.

The susceptibility of Mg alloys to corrosion can be influenced by the presence of amino acids. However, the change in susceptibility is dependent on the types of amino acids present. Amino acids exhibit either acid-base/polar or non-polar properties. For example, cysteine (C) is neutral/slightly polar, glutamine (Q) is neutral/polar, and tryptophan (W) is neutral/slightly polar.

TABLE 3

Average potentiodynamic polarization data for mechanically polished samples in PBS at 37° C.

| Samples (MP) | $E^{corr}$ (V) | $I^{corr}$ (µA) | Corr Rate (mm/year) |
|---|---|---|---|
| Mg1Zn (ACI) | −1.4 | 2.8E−4 | 2.4 |
| Mg1Zn1Ca (ACI) | −1.7 | 6.3E−4 | 19.5 |
| Mg1Zn1Ca8Gd (ACI) | −1.6 | 5.3E−4 | 27.8 |
| Mg1Zn1Ca | −1.7 | 57.30 | 2.9 |
| Mg1Zn1Ca1HA | −1.5 | 159.0 | 26.4 |
| Mg1Zn1Ca3HA | −1.6 | 155.0 | 16.0 |
| Mg5Zn1Ca | −1.2 | 26.40 | 10.9 |
| Mg5Zn1Ca1HA | −1.5 | 36.90 | 2.6 |
| Mg5Zn1Ca3HA | −1.6 | 148.0 | 15.1 |

TABLE 4

Average potentiodynamic polarization data from three test values in PBS and PBS containing amino acids.

| Samples, MP | $E^{corr}$ (V) | $I^{corr}$ (µA) | Corr Rate (mm/year) |
|---|---|---|---|
| Mg1Zn, PBS | −1.43 | 2.8E−4 | 2.42 |
| Mg1Zn, PBS + C | −1.68 | 7.87E−04 | 64.3 |
| Mg1Zn, PBS + Q | −1.48 | 13.21E−04 | 107.83 |
| Mg1Zn, PBS + W | −1.73 | 15.95E−04 | 130.11 |
| Mg1Zn1Ca, PBS | −1.68 | 6.30E−4 | 19.46 |
| Mg1Zn1Ca, PBS + C | −1.72 | 4.70E−04 | 37.89 |
| Mg1Zn1Ca, PBS + Q | −1.61 | 4.15E−04 | 33.89 |
| Mg1Zn1Ca, PBS + W | −1.65 | 3.45E−04 | 28.14 |
| Mg1Zn1Ca8Gd, PBS | −1.56 | 5.3E−4 | 27.78 |
| Mg1Zn1Ca8Gd, PBS + C | −1.61 | 19.69E−04 | 163.93 |
| Mg1Zn1Ca8Gd, PBS + Q | −1.59 | 5.89E−04 | 49.01 |
| Mg1Zn1Ca8Gd, PBS + W | −1.63 | 18.67E−04 | 155.56 |

Example 2—Electrochemical Impedance Spectroscopy (EIS)

Figure 4:
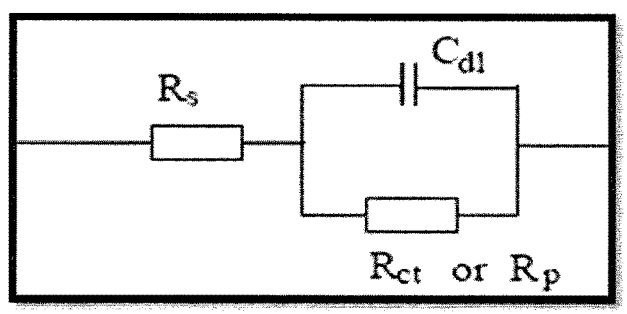
FIG. 4 shows an equivalent circuit of the corrosion cell, where $R_s$ is electrolyte resistance, $R_{ct}$ is charge transfer resistance, and $C_{dl}$ is capacitance double layer.
Figure 5:
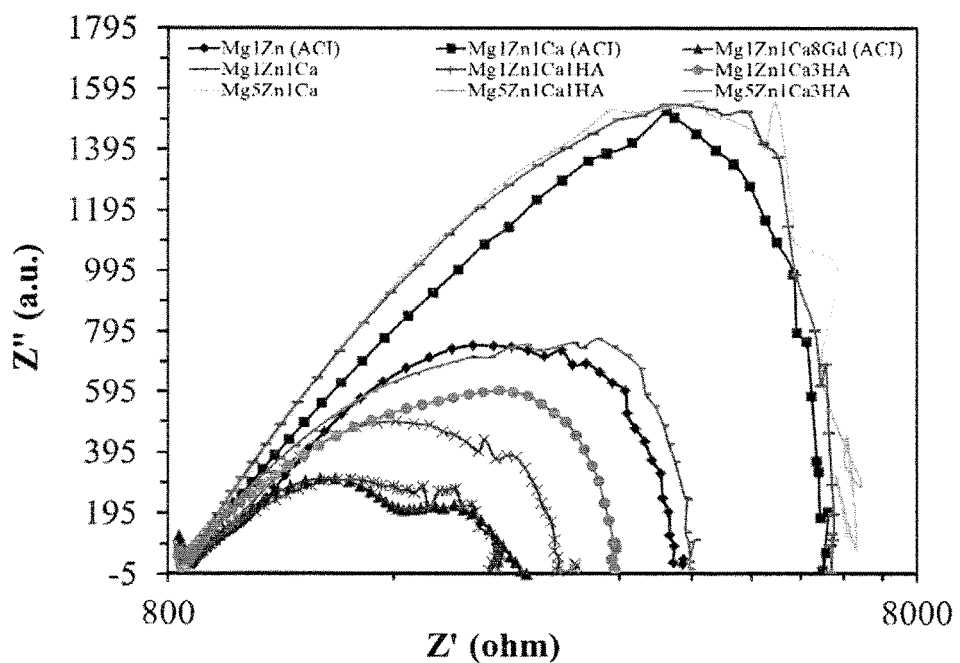
FIG. 5 demonstrates Nyquist plots (log-log representation) for mechanically polished samples in PBS at 37° C.

The interphase between liquid and solid media can be described in terms of an electrical circuit with resistors and capacitors. FIG. 4 shows the Randles equivalent circuit, where $R_s$ is the electrolyte resistance, $R_{ct}$ is the charge transfer resistance, and $C_{dl}$ is the capacitance double layer. FIG. 5 shows the Nyquist plots for mechanically polished alloys in PBS. The impedance of MgZn increased with the addition of Ca, Gd, and HA. This could be attributed to the formation of various oxides, which act as an electric barrier. In the case of biodegradable alloys, an initial slower corrosion rate followed by uniform degradation are desirable. Mg5Zn1Ca, Mg5Zn1Ca3HA and Mg1Zn1Ca (ACI) exhibited higher charge transfer resistance (Ret) as compared with the rest of the samples, which ranged between 2300 ohm and 6500 ohm. The capacitive arc provides an estimate of corrosion resistance of the material, in terms of its relative diameter, which is directly proportional to the charge transfer resistance ($R_{ct}$). Thus, an increase in semi-circle diameter corresponds to an increase in corrosion resistance.

Each mechanically polished sample displayed an inductive loop at low frequencies, which signified that the samples were susceptible to pitting corrosion. No second capacitive loop was observed. This occurs when Cl⁻ ions diffuse through a breach in the passivating layer, resulting in the formation of hydrolyzed metal chlorides. Pitting corrosion can deteriorate the properties of an implant, as would the presence of various organic components in the physiological solution. Additionally, an increase in concentration of dissolved ions compresses the electrical double layer, which increases the zeta potential (Orazem M E, Tribollet B. Electrochemical Impedance Spectroscopy. John Wiley & Sons, Hoboken, N.J., 2008).

Figure 6:
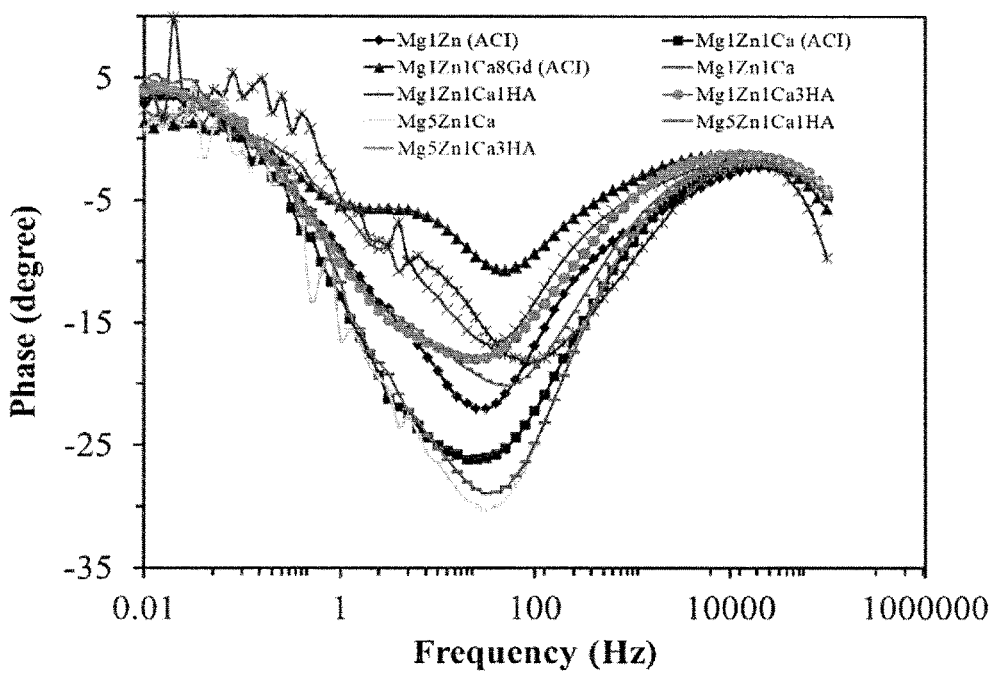
FIG. 6 shows Bode plots (phase vs. frequency) for mechanically polished alloys in PBS at 37° C.

The Bode plot for mechanically polished Mg alloys in PBS at 37° C. is illustrated in FIG. 6. The degree of phase shift is a function of the type and proportion of oxides produced on the surface of the alloy. The phase shift at a frequency of approximately 80 Hz is most likely due to an increase in surface film capacitance, which is dependent on the oxide layers produced on the surface. The symmetry of the Bode plot is an indication of the uniformity of the surface oxide coverage. The magnitude of the phase shift is a measure of the resistance to corrosion (impedance). When the loop is depressed and shifts towards a higher frequency, adsorption and desorption phenomena occur on the surface of the samples. Mg1Zn1Ca8Gd and Mg1Zn1Ca1HA showed a phase shift towards higher frequency of approximately 100 Hz, which is due to the adsorption phenomenon. For example, deposition of a layer of corrosion products and salt deposits from the solution could reduce the degradation rate of the alloy and impart long-term stability in a biological environment.

Figure 7:
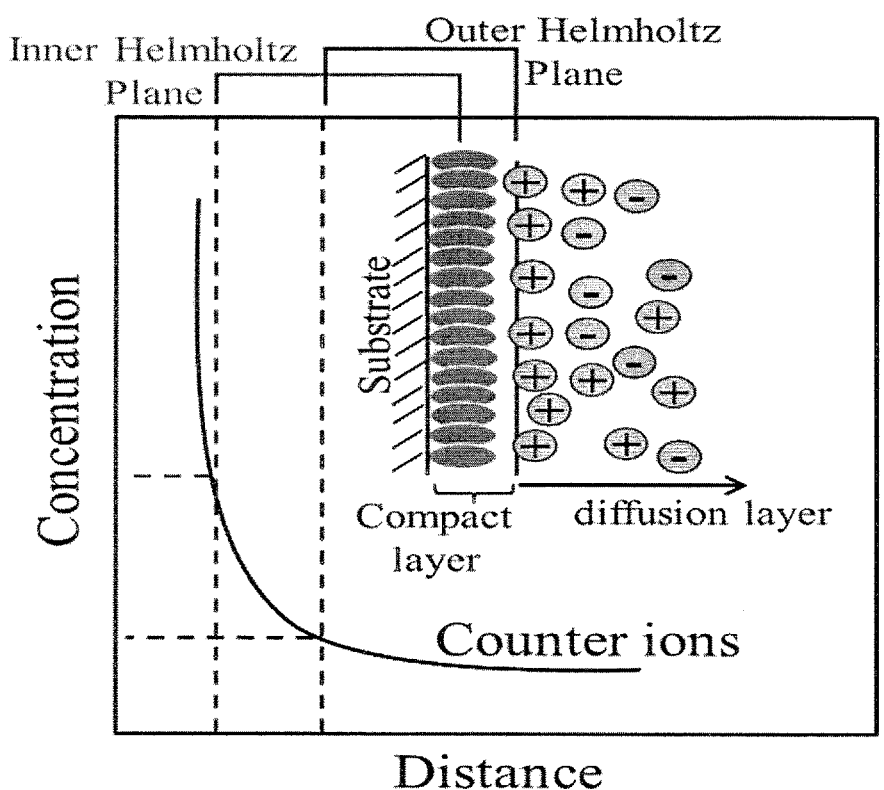
FIG. 7 depicts changes in the concentration of counter ions with varying distance from the surface.
Figure 8:
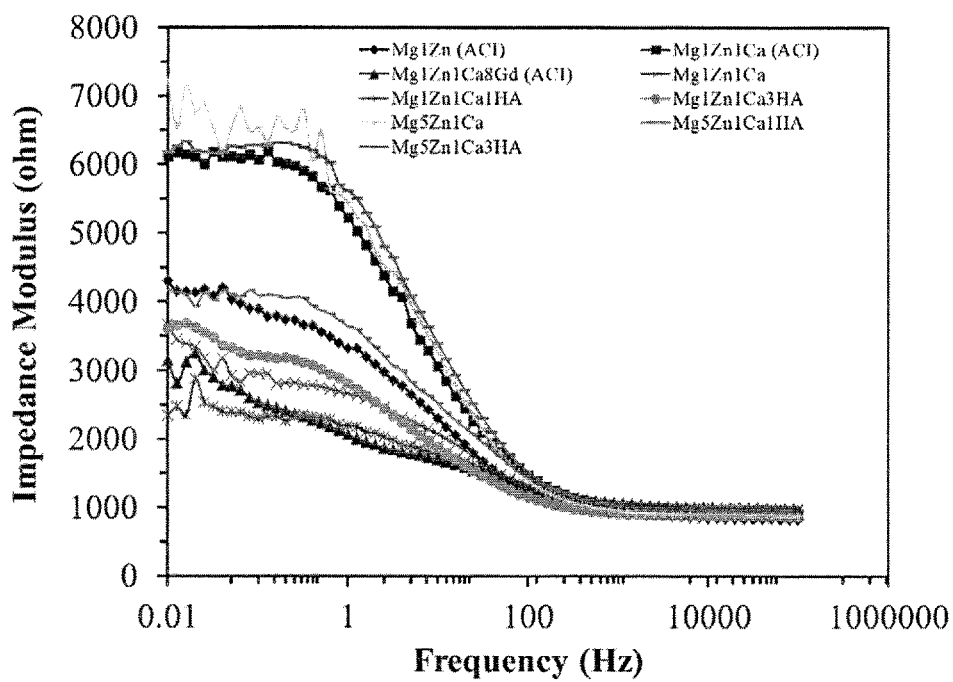
FIG. 8 shows the Bode plots (impedance modulus vs. frequency) of mechanically polished alloys in PBS at 37° C.

Impedance is defined as the ratio of the voltage phasor to the electric current phasor. An increase in concentration of ions in solution decreases impedance modulus value, which will compress the double layer as shown in FIG. 7. FIG. 8 shows the impedance modulus loop, where the low frequency domain represents the system resistance, which mainly depends on polarization resistance of the passivating film and the double layer capacitance of the electrode, while the high frequency domain represents the solution resistance ($R_s$).

Example 3—Immersion and Dynamic Immersion Test

Figure 9:
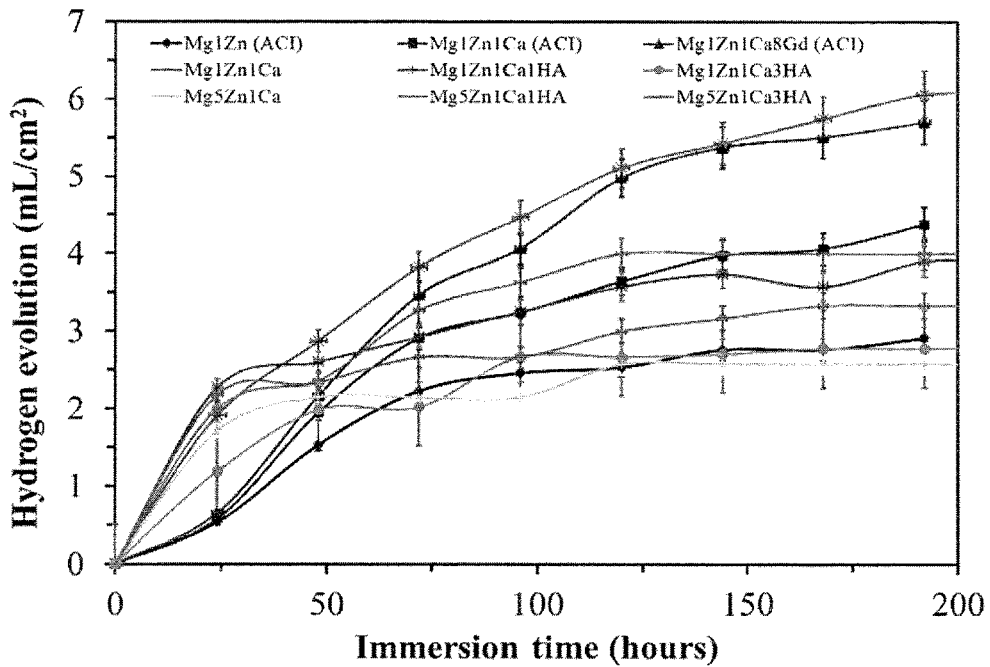
FIG. 9 demonstrates the volume of hydrogen evolution from mechanically polished samples immersed in PBS for 192 hours at 37° C.

FIG. 9 shows the volume per unit surface area of hydrogen evolution as a function of time from mechanically polished samples. A similar volume of hydrogen was released during the initial 24 hours but a greater volume of hydrogen was evolved from the mechanically polished alloys after 150 hours. In the case of mechanically polished samples, Mg1Zn1Ca and Mg1Zn1Ca8Gd displayed the highest hydrogen evolution (190 hours), a similar behavior was observed in the potentiodynamic polarization results provided herein. Higher hydrogen evolution in the latter is due to inhomogeneous distribution of Gd in the matrix, and for Mg1Zn1Ca is mainly from the formation of less stable porous oxides.

Figure 10:
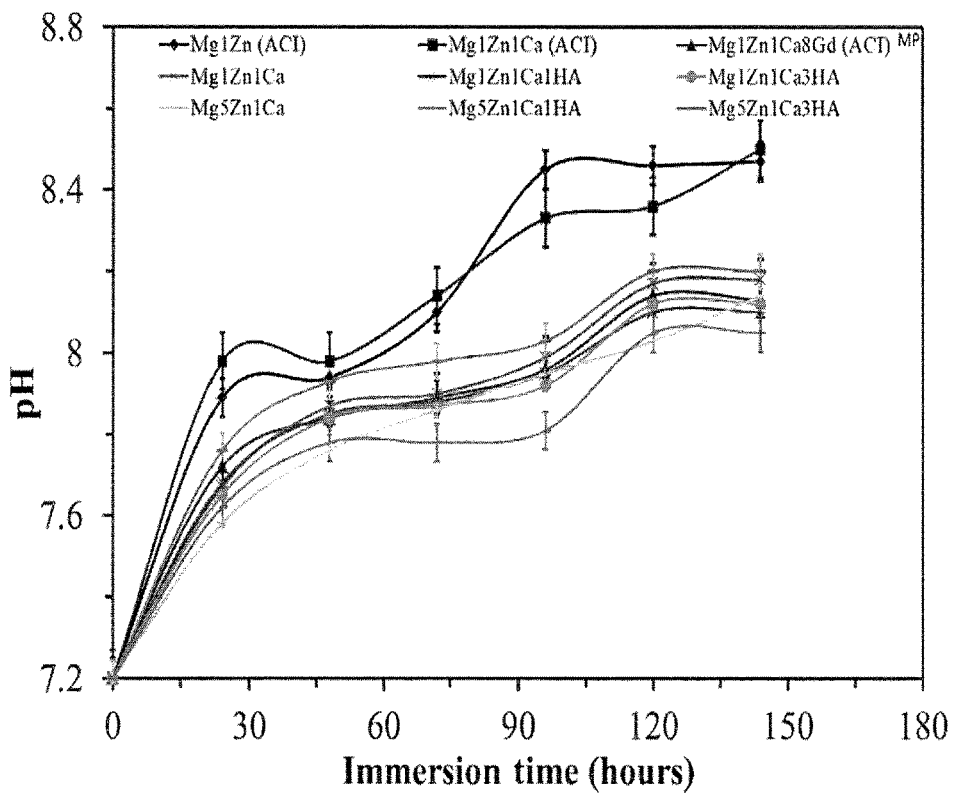
FIG. 10 shows the pH of mechanically polished samples immersed in PBS at 37° C.

The pH of the PBS was monitored during an immersion test using a Thermo Orion model#420 A+ pH meter. The pH was approximately 7.2-8.4 for the mechanically polished samples and approximately 7.2-7.5 for anodized samples, the latter having greater passivation. FIG. 10 and shows the pH values for mechanically polished in PBS at 37° C. Due to poor passivation Mg1Zn showed the highest increase in pH. Wang et al. reported the precipitation of less soluble products, such as $Mg_3(PO_4)_2$, magnesium apatite, zinc phosphate, and calcium phosphate due to a local increase in pH (Wang Y, Lim C S, Lim C V, Yong M S, Teo E K, Moh L N. In vitro degradation behavior of MIA magnesium alloy in protein-containing simulated body fluid. Materials Science and Engineering C, 2011; 31:579-587).

The corrosion resistance of biodegradable Mg alloys is influenced by several factors. Some of the factors considered during in-vitro tests included simulated body fluids and human body temperature, 37° C. Table 5 shows the corrosion rates of mechanically polished Mg samples after immersion in PBS at 37° C. for 192 hours. The mechanically polished samples exhibited a higher susceptibility to corrosion. Similar corrosion behavior was also observed with potentiodynamic polarization experiments as shown herein. Furthermore, the addition of HA to MgZnCa increased the rate of corrosion due to porosity, cracking, and delamination of the oxides.

TABLE 5

Corrosion rates depicted for mechanically polished samples via immersion test

| Mechanically Polished Alloys | Corr. Rate (mm/year) |
| --- | --- |
| Mg1Zn (ACI) | 0.3 |
| Mg1Zn1Ca (ACI) | 0.5 |
| Mg1Zn1Ca8Gd (ACI) | 0.6 |
| Mg1Zn1Ca | 2.4 |
| Mg1Zn1Ca1HA | 3.4 |
| Mg1Zn1Ca3HA | 2.6 |
| Mg5Zn1Ca | 2.5 |
| Mg5Zn1Ca1HA | 2.3 |
| Mg5Zn1Ca3HA | 3.1 |

Figure 11:
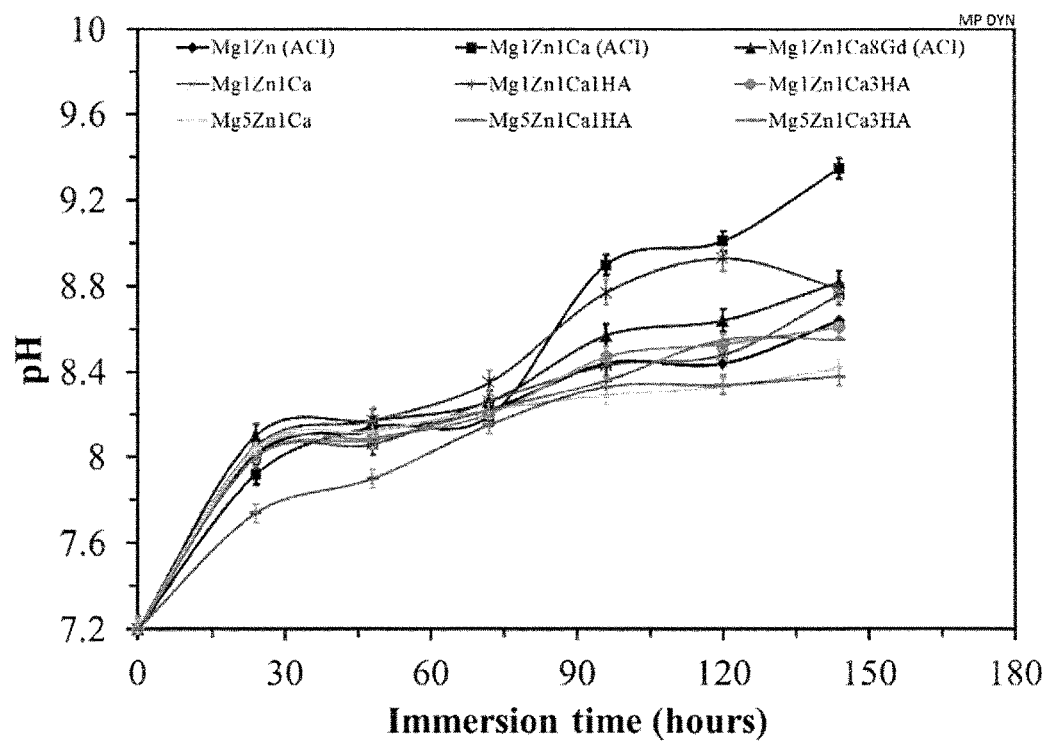
FIG. 11 shows the pH of mechanically polished samples under dynamic immersion in PBS at 37° C.

In order to better understand the degradation behavior of the alloys, dynamic immersion tests were performed on a vortex shaker with a constant speed of approximately 500 rpm for 144 hours in PBS at 37° C. Due to the nature of the test setup, it was not feasible to determine the hydrogen evolved. Relatively higher increase in pH and corrosion rate were observed under dynamic immersion tests for both mechanically polished samples as compared to those obtained with static immersion tests. The pH monitored during dynamic immersion for mechanically polished samples ranged between 7.2 and 9.3 (FIG. 11).

Table 6 shows the corrosion rates (dynamic immersion tests) of mechanically polished Mg samples in PBS at 37° C. During dynamic immersion testing, constant movement of the electrolyte prevents the corrosion products from accumulation on the surface and the degradation rate is much faster than that under static conditions. The nature of corrosion damage under static immersion was mainly localized, whereas during dynamic immersion the corrosion was nearly uniform.

TABLE 6

Corrosion rates depicted from dynamic immersion test for mechanically polished samples

| Samples | Mechanically Polished (m/year) |
| --- | --- |
| Mg1Zn (ACI) | 1.08 |
| Mg1Zn1Ca (ACI) | 0.58 |
| Mg1Zn1Ca8Gd (ACI) | 0.98 |
| Mg1Zn1Ca | 1.22 |
| Mg1Zn1Ca1HA | 3.18 |
| Mg1Zn1Ca3HA | 3.81 |
| Mg5Zn1Ca | 3.27 |
| Mg5Zn1Ca1HA | 2.99 |
| Mg5Zn1Ca3HA | 2.26 |

Example 4—Mechanical Studies

Reliable results can be obtained by the Oliver-Pharr method when the ratio of $h_f/h_{max}$ is less than 0.7, where $h_f$ is the final displacement at complete unloading and $h_{max}$ is the maximum depth of penetration during a nanoindentation test (Bolshakov A, Pharr G M. Influences of pileup on the measurement of mechanical properties by load and depth sensing indentation techniques. J. Mater. Res., 1998; 13:1049-1058). This approach does not account for possible pile-up behavior. The alloys exhibited mainly plastic behavior, where the values for the bulk sample (depths above 1000 nm and peak loads above 25 mN) were relatively constant with indentation depth in excess of 1000 nm. However, an increase in the modulus was observed with the addition of alloying elements. Due to the possibility of the formation of oxides on the surface, in this investigation the indentation data at shallow depths was not determined.

Figure 12A:
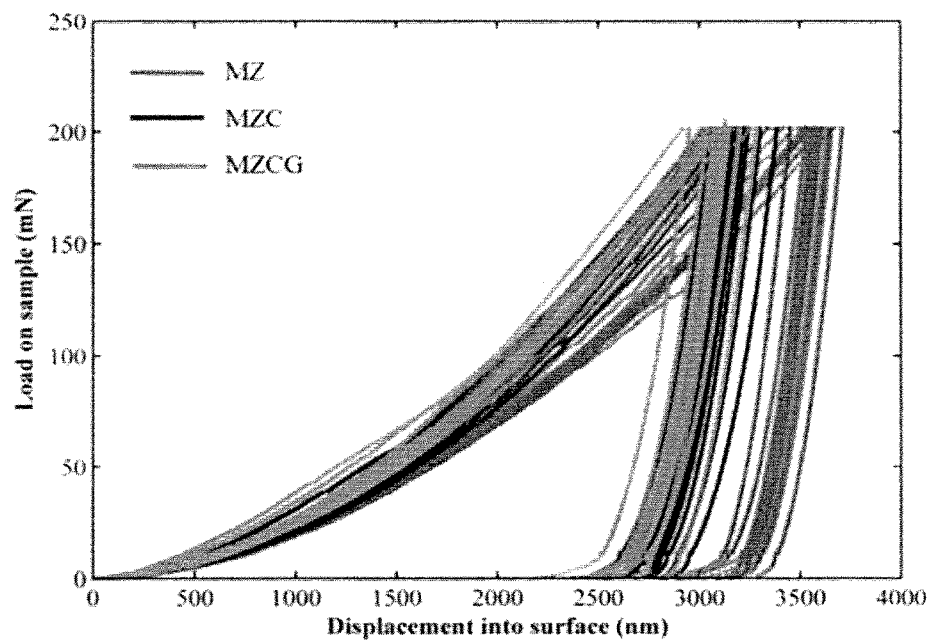
FIGS. 12A-12C show the results of nanoindentation experiments. 12A shows a typical load vs. displacement curves for 200 mN peak load. 12B shows peak load vs. modulus in Mg1Zn, Mg1Zn1Ca and Mg1Zn1Ca8Gd. 12C shows peak load vs. modulus in Mg1Zn1Ca, Mg1Zn1Ca1HA, Mg1Zn1Ca3HA, Mg5Zn1Ca, Mg5Zn1Ca1HA and Mg5Zn1Ca3HA.
Figure 12B:
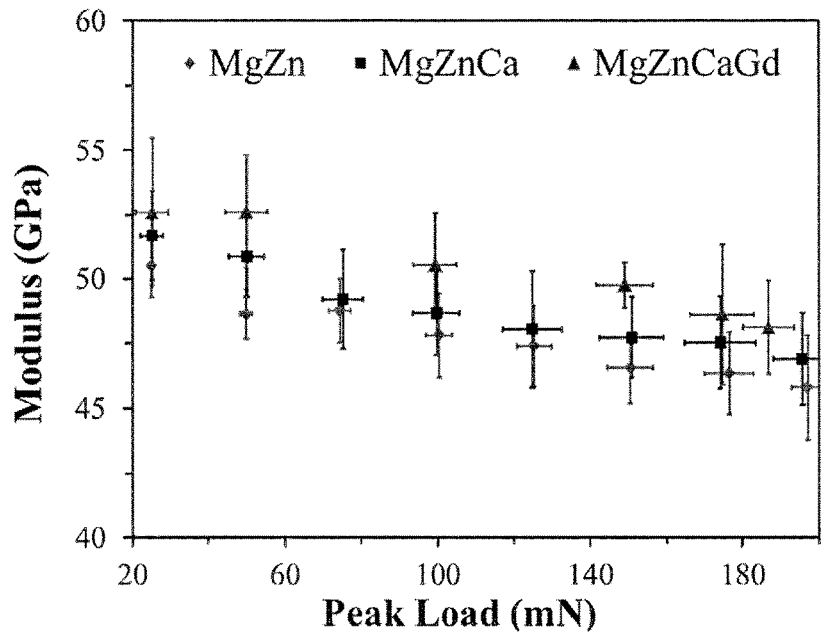
Figure 12C:
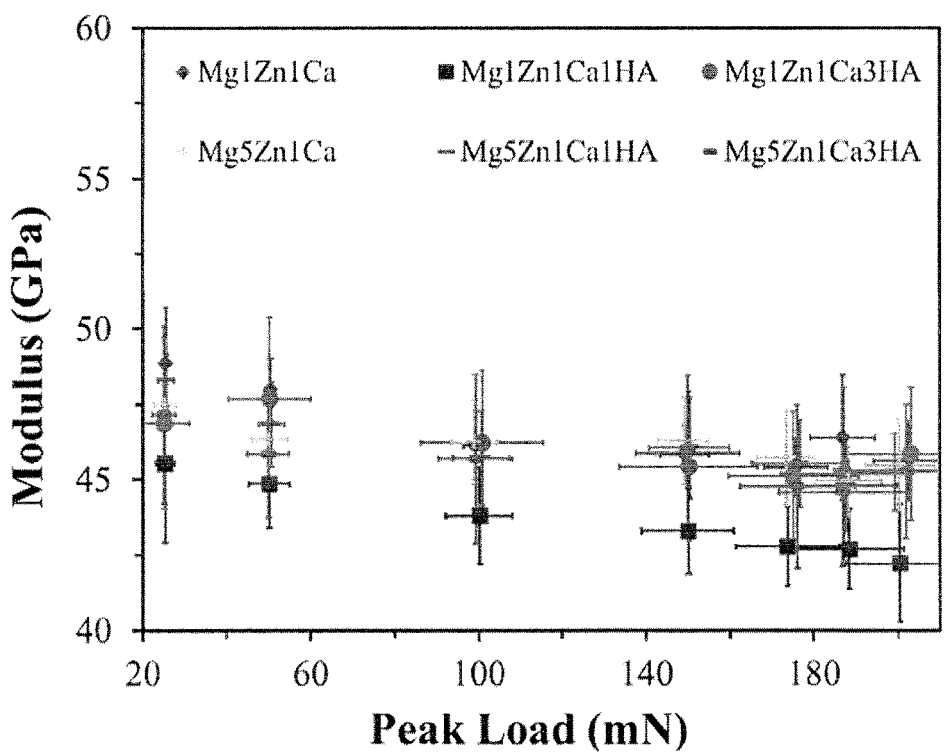
Figure 13A:
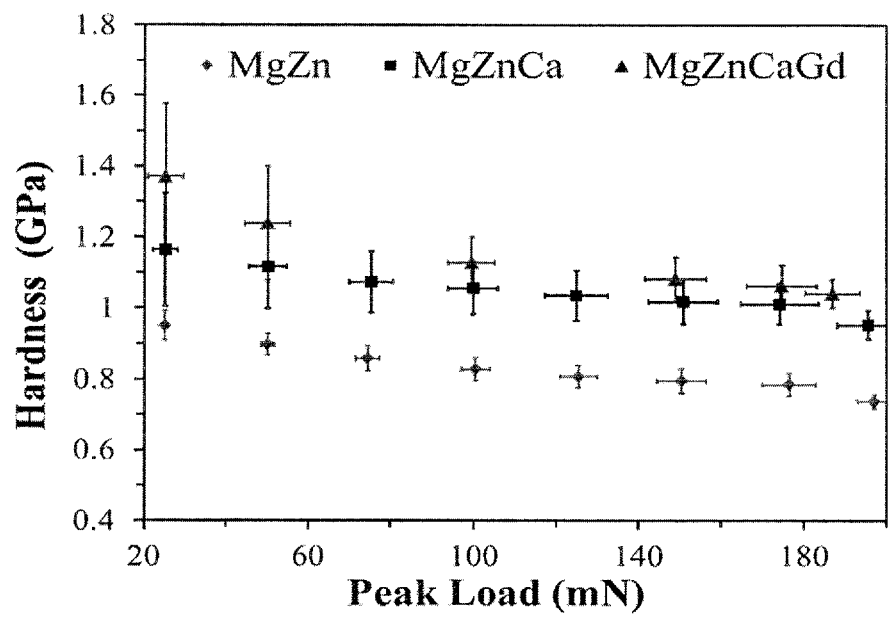
FIGS. 13A-13B demonstrate the hardness values calculated by the Oliver Pharr approach for Mg1Zn, Mg1Zn1Ca and Mg1Zn1Ca8Gd (13A) and Mg1Zn1Ca, Mg1Zn1Ca1HA, Mg1Zn1Ca3HA, Mg5Zn1Ca, Mg5Zn1Ca1HA and Mg5Zn1Ca3HA (13B).
Figure 13B:
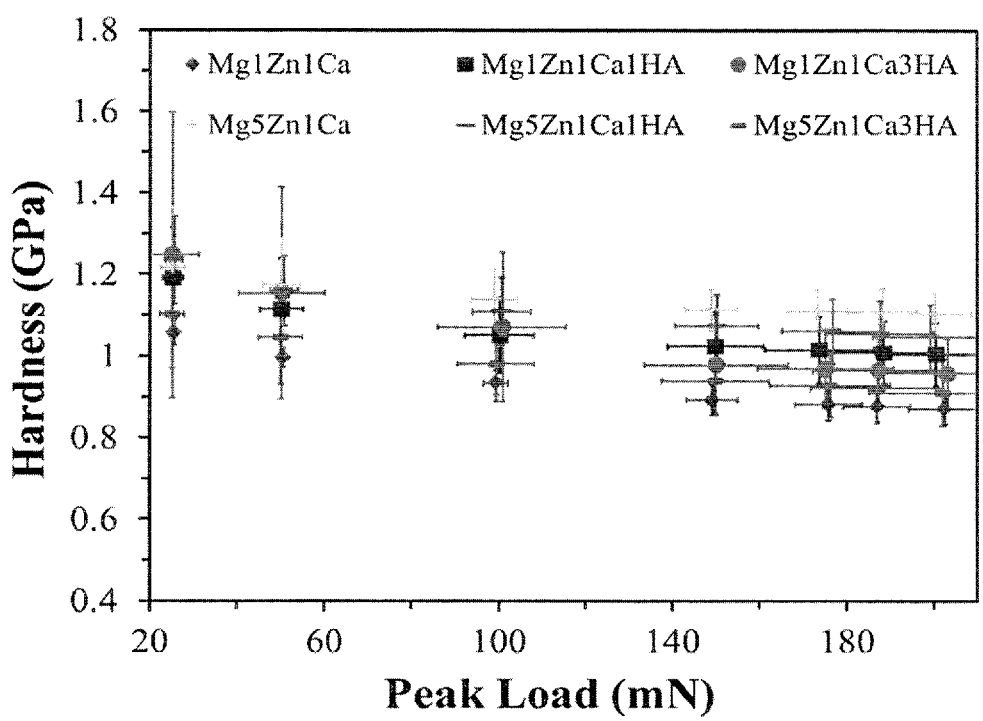
Figure 14:
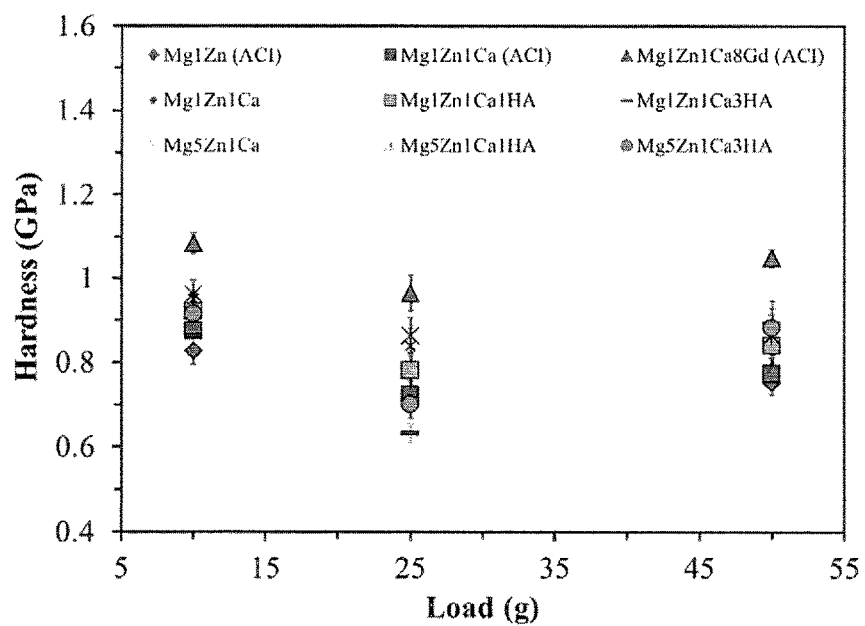
FIG. 14 shows the load vs. hardness values calculated from Vicker's hardness.

Because the grain-sizes of the samples were greater than 60 microns, only data obtained at depths greater than 1000 nm were considered as bulk properties of the material. The hardness and the modulus of the specimens remained almost constant at depths greater than 1000 nm. As shown in FIGS. 12A-12C, MgZnCaGd had the highest modulus (approximately 52 GPa) and hardness (approximately 1.2 GPa) followed by MgZnCa/nHA (the modulus was between 45 GPa and 50 GPa, hardness between 0.8 GPa and 1.1 GPa). This can be attributed to the segregation of Zn, Ca, and HA in MgZnCa/nHA and Zn, Ca, Gd in MgZnCaGd at the grain boundaries, where Zn, Ca, and HA act as a grain-refining agents and contribute to solid solution formation, precipitation, and grain boundary strengthening. Gd improved the strength and creep resistance of Mg alloys, and Zn, along with other alloying elements, improved the strength and corrosion resistance of Mg (Avedesian M M, Baker H. Magnesium and magnesium alloys. ASM International Handbook, 1999). The average displacement curves of the MgZn, MgZnCa and MgZnCaGd specimens show an increase in the work of indentation or the hysteresis loop energy with the addition of Ca to MgZn, which further increased in the samples comprising Gd. The hardness was calculated from the Nanoindentation results (FIGS. 13A-13B) and the Vicker's hardness (FIG. 14) results were comparable and ranged from 0.7 GPa to 1.4 GPa. Mg1Zn and Mg1Zn1Ca exhibited the lowest hardness of approximately 0.8 GPa, which increased with the addition of Gd and Zn to MgZnCa to approximately 1.2 GPa.

Figure 15:
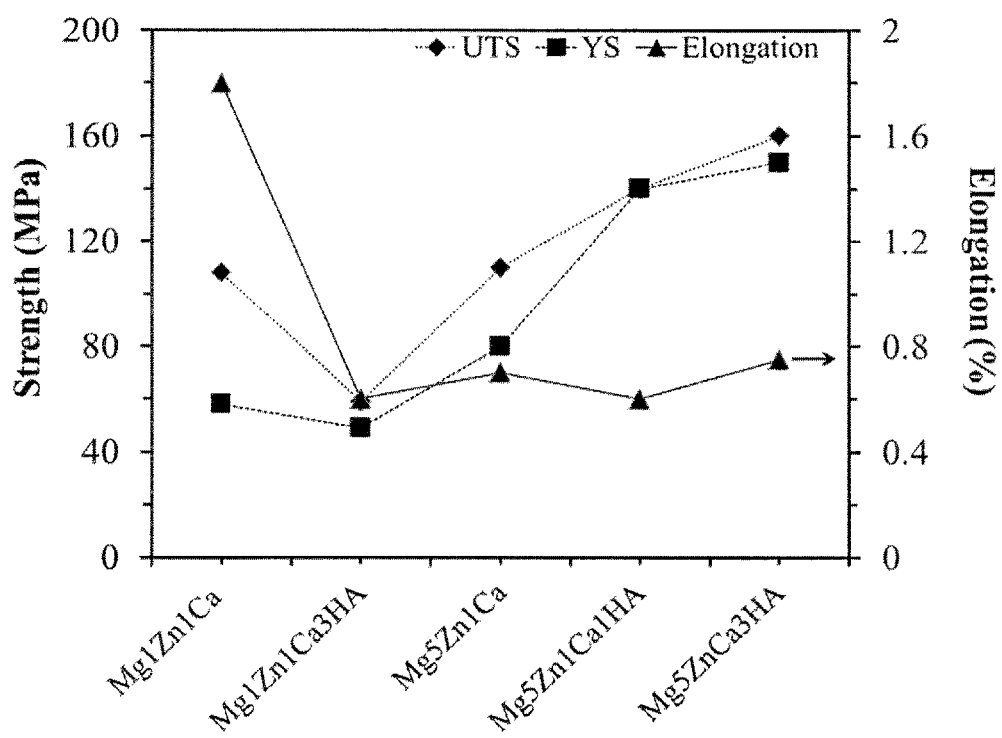
FIG. 15 demonstrates the approximate tensile properties of certain alloys.
Figure 16A:
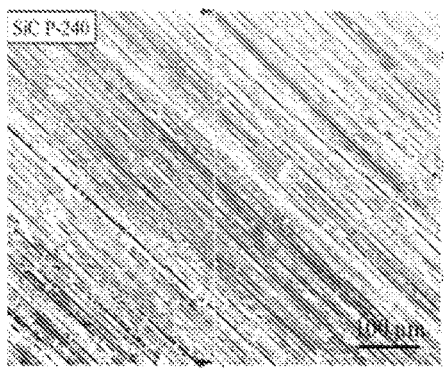
FIG. 16 provides interference microscope images Mg1Zn1Ca with a scan area of 640 μm×860 μm after being polished by SiC-240 (16A), SiC P-320 (16B), SiC P-400 (16C), and C-DP 0.05 μm (16D).
Figure 16B:
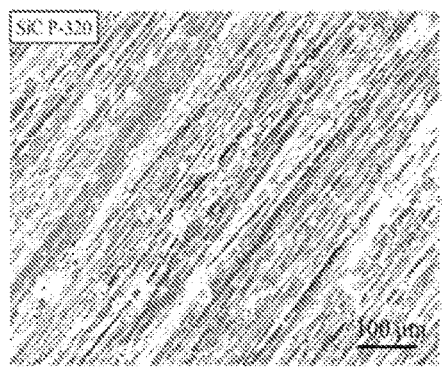
Figure 16C:
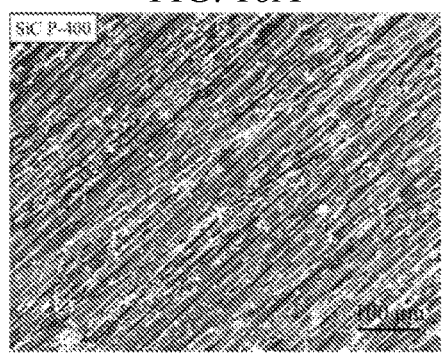
Figure 16D:
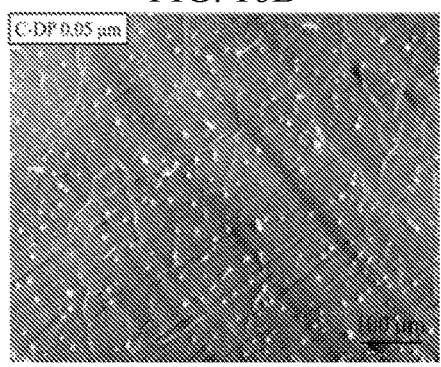
Figure 17A:
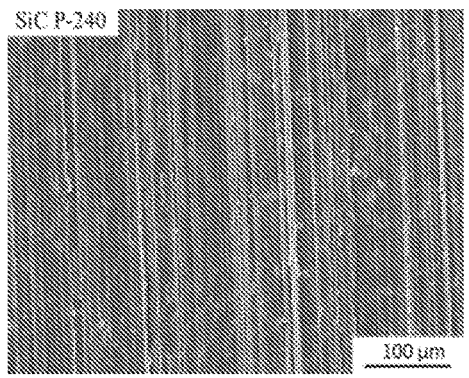
FIG. 17 provides SEM micrographs of Mg1Zn1Ca alloys with different surface roughness after being polished by SiC-240 (17A), SiC P-320 (17B), SiC P-400 (17C), and C-DP 0.05 μm (17D).
Figure 17B:
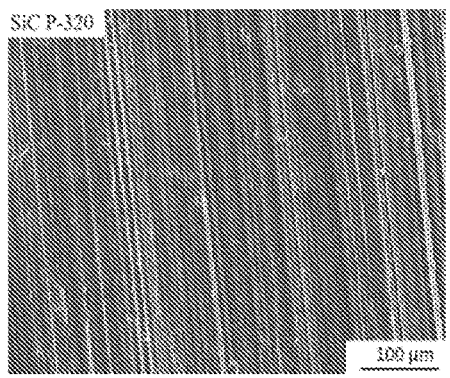
Figure 17C:
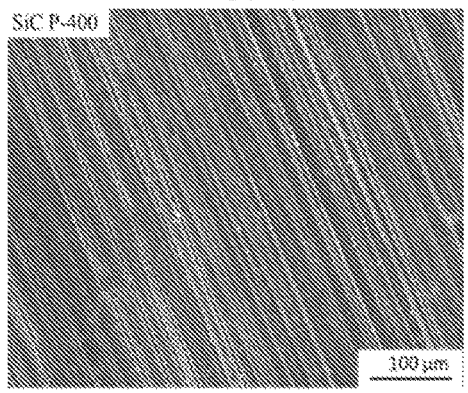
Figure 17D:
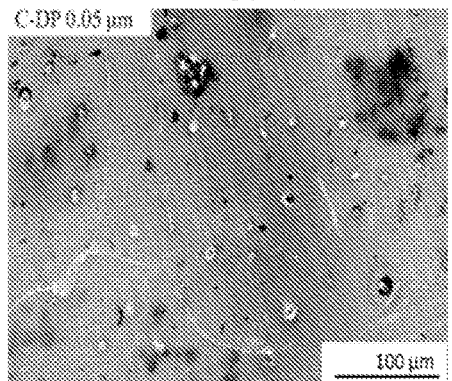

In comparison with biodegradable Mg alloys, polymers possess much lower mechanical strength and hardness (Ye X, Chen M, Yang M, Wei J, Liu D. In vitro corrosion resistance and cytocompatibility of nano-hydroxyapatite reinforced Mg—Zn—Zr composites. J Mater Sci: Mater Med. 2010; 21:1321-1328; Kubásek J, Vojtěch D. Mechanical properties and corrosion behavior of biodegradable magnesium alloys. Metal, 2011; 18:1-6). Therefore, Mg-based biodegradable alloys are more suitable for load-bearing applications. The mechanical properties of Mg alloys are similar to that of human bone, which can help avoid stress shielding. Zibiao Li (2010) reported the strength and elongation percentage of Mg samples with selective compositions as shown in FIG. 15 (Li Z. Mg/Hydroxyapatite composites for potential bio-medical applications, M. Phil, Brunel University, Brunel Center for Advanced Solidification Technology (BCAST), August 2010).

The results indicate that the tensile strength of MgZnCaHA was influenced by both Zn and HA content. The addition of Zn and HA restrict grain growth, which can further improve the alloys' mechanical properties. According to the Hall-Petch equation there is an inverse relationship between grain size and yield strength; in this case yield strength increased with reduced grain size.

The tensile and yield strength improved with the addition of HA, which could be due to the load transfer in metal matrices (Li Z. Mg/Hydroxyapatite composites for potential bio-medical applications, M. Phil, Brunel University, Brunel Center for Advanced Solidification Technology (BCAST), August 2010). It was reported that the fluctuation in the elongation data was due to microstructural defects.

Example 5—Surface Roughness Characterization

Contact angle (CA), surface free energy (SFE), fractional polarity (FP), and corrosion rate (CR) were compared between surfaces having different roughness. As-cast Mg1Zn1Ca (wt %) alloys were mechanically polished to various degrees of surface roughness. Electrochemical techniques (potentiodynamic and EIS) and wettability tests were performed to study the influence of surface roughness on electrochemical passivation and surface free energy, respectively. Furthermore, microstructure and surface morphology of the alloys were assessed using scanning electron microscopy/energy-dispersive X-ray spectroscopy (SEM/EDS).

Ingots of Mg1Zn1Ca were prepared and mechanically polished according to procedures provided herein. Instead of water, ethanol was used with SiC and a mixture of ethanol:ethylene glycol (3:1) with diamond paste was used on the carbimet surface. The surface roughness of the alloys was determined by optical profilometer and the data was analyzed by Scanning Probe Image Processor (SPIP).

PBS (Sigma Aldrich) was used as the standard test solution for electrochemical studies. Potentiodynamic polarization and EIS tests were performed at 37° C. in accordance with ASTM G 102-89 and ASTM G 3-89, respectively. Potentiodynamic polarization tests were conducted at a scan rate of 1.0 mV/s. The electrolyte was purged with high purity nitrogen for 30 minutes prior to immersion of the sample, as well as continuously during the corrosion test. Faraday's law was used to calculate the corrosion rate (CR), in terms of penetration rate of the alloys, determined by Equation (5) below:

$$CR=(I_{corr} \cdot K \cdot EW)/(\rho \cdot A) \quad (5)$$

where $I_{corr}$ is the corrosion current (amps), K is a constant for the corrosion rate (3272 mm/amp·cm·year), EW is the equivalent weight in grams/equivalent, A is the sample area (0.28 cm$^2$) and $\rho$ is the density (1.69 g/cm$^3$) of the alloy calculated by Archimedes principal.

EIS tests were also conducted in PBS under high purity nitrogen and in the frequency range from 1.0E−02 Hz to 1.0E+05 Hz with 10 points per decade to determine the effect of alloying elements on the charge transfer resistance.

Contact angles and surface free energy were measured using a Kyowa contact angle meter model DM-CE1 and adopting the sessile drop method. Surface morphologies of the alloys were studied by scanning electron microscopy (SEM, JEOL JSM 6330F), at an accelerated voltage of 20 kV.

Figure 21:
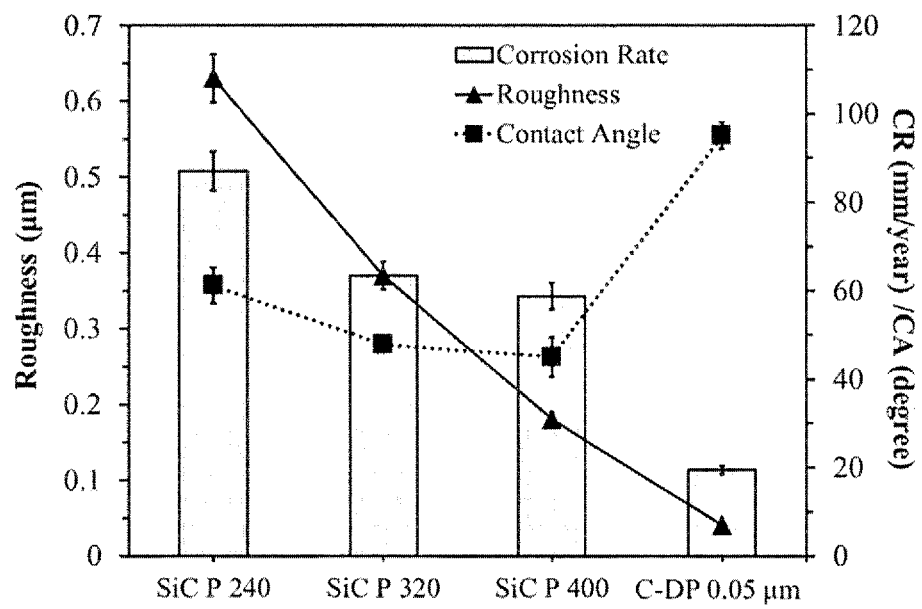
FIG. 21 is a plot showing the effects of roughness on corrosion rate (CR) and contact angle (CA) after polishing with four different abrasives.

FIG. 21 compares the contact angle (CA) and corrosion rate (CR) parameters at different surface roughness. An increase in contact angle was observed with a decrease in surface roughness, where it shifted from hydrophilic to hydrophobic (CA changed from 44° to 95°). The surface free energy (mJ/m$^2$) components were calculated by using Kitazaki-Hata theory (Equation (6) below):

$$\gamma^{total}=\gamma^d+\gamma^p+\gamma^h \quad (6)$$

where $\gamma^{total}$ is the total SFE, $\gamma^d$ is the dispersion component of the SFE, $\gamma^p$ is the polar component of the SFE, and $\gamma^h$ is the hydrogen bond component of the SFE.

Three liquids of different surface tensions (water, ethylene-glycol and diiodomethane) were used under ambient conditions. The SFE for 0.05 μm surface finish was 29.7 mJ/m$^2$, whereas at a higher roughness it ranged between 88.0 mJ/m$^2$ to 96.0 mJ/m$^2$ (Table 7). Studies have shown that cellular adhesion and cell activity are favorable on materials with low SFE (~25-35 mJ/m$^2$). Furthermore, fractional polarity (FP) was calculated, where Fractional Polarity=polar/(polar+dipersion). It was previously reported that a fractional polarity of less than 0.3 is a favorable parameter for good cellular adhesion. In this study, a decrease in FP from 0.13 to 1.0 was observed with decreased roughness. Therefore, lower roughness is conducive to improved biocompatibility.

TABLE 7

Surface free energy and fractional polarity components

| Sample | SFE (mJ/m$^2$) | Fractional polarity, FP |
|---|---|---|
| SiC P 240 | 88 | 0.79 |
| SiC P 320 | 184.5 | 0.97 |
| SiC P 400 | 96 | 0.79 |
| C-DP 0.05 μm | 29.7 | 0.13 |

Example 6—Effects of Surface Roughness on Corrosion Resistance

Table 8 shows the surface roughness ($S_a$) and roughness mean ($S_{mean}$) values obtained from the optical profilometer. A decrease in surface roughness was observed with an increase in grit size of the grinding surface. FIGS. 16A-16D and FIGS. 17A-17D show the images of the alloy surfaces prepared at various roughness measurements. A decrease in size and density of pores and scratches were observed with decreasing surface roughness.

TABLE 8

Lubricants and abrasives used during sample preparation and average roughness parameters

| Sample Finish | Lubricant | $S_a$ (μm) | $S_{mean}$ (μm) |
|---|---|---|---|
| SiC P-240 | Ethanol | 0.63 | −1.33 |
| SiC P-320 | Ethanol | 0.37 | −0.14 |
| SiC P-400 | Ethanol | 0.18 | 0.24 |
| C-DP 0.05 μm | Ethanol-Ethylene Glycol (3:1) | 0.04 | −0.08 |

Figure 18:
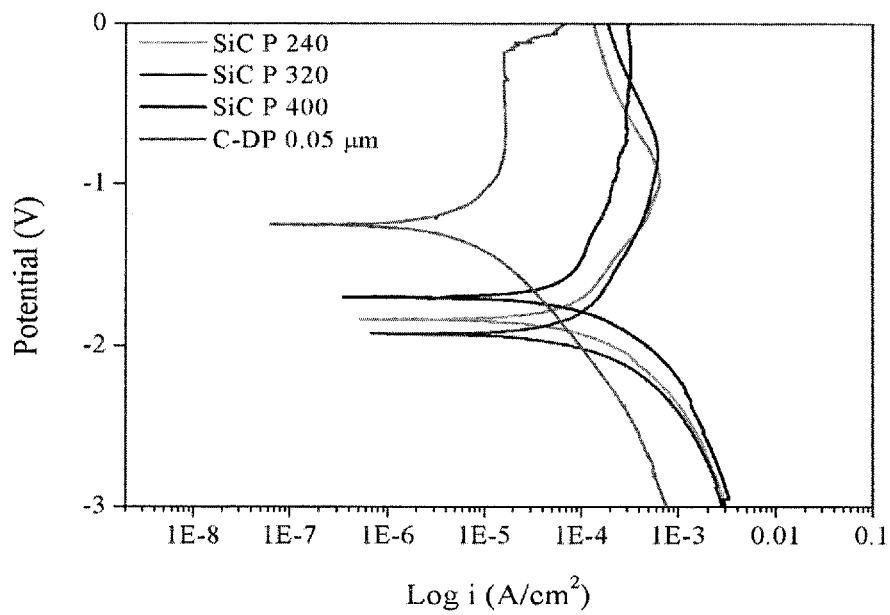
FIG. 18 shows the potentiodynamic polarization curves of Mg1Zn1Ca alloys at different roughness in PBS at 37° C.

The potentiodynamic polarization corrosion and EIS tests were performed in PBS at 37° C. Table 9 summarizes the corrosion parameters, where the corrosion rate and corrosion current ($I_{corr}$) decreased with a decrease in surface roughness. This corresponded to a shift of the corrosion potential ($E_{corr}$) in a more noble direction rates with decrease in roughness. The sample with lowest surface roughness of 0.04 μm had a corrosion potential of −1.2 V (vs. SCE); whereas that of the other samples ranged between −1.7 V to −1.9 V. The corrosion current decreased from 48.4 μA to 6.8 μA as the roughness decreased from 0.63 μm to 0.04 μm. Potentiodynamic plot of the sample with lowest roughness (C-DP 0.05 μm) initially displayed distinct passivation as evidenced by the vertical straight line of the anodic curves (FIG. 18). Furthermore, polarization resistance ($R_p$) which evaluates the protective behavior of the surface was calculated using the following formula (Equation (7) below):

$$R_p = \beta_a \beta_c / 2.3 \cdot I_{corr}(\beta_a - \beta_c) \quad (7)$$

where $\beta_a$ and $\beta_c$ are anodic and cathodic slopes, respectively. $R_p$ increased with decreasing roughness, due to the formation of a relatively uniform and compact oxide layer. This behavior was further confirmed with the EIS plots. The increased may be attributed to the formation of mixed oxides of Mg and Zn.

TABLE 9

Results of potentiodynamic corrosion tests of the samples in PBS at 37° C.

| Sample Finish | $E_{corr}$ (V) | $I_{corr}$ (μA) | $R_p$ (Ωcm²) | CR (mm/year) |
|---|---|---|---|---|
| SiC P 240 | −1.8 | 48.4 | 114.5 | 87.1 |
| SiC P 320 | −1.9 | 35.3 | 107.9 | 63.4 |
| SiC P 400 | −1.7 | 32.7 | 136.5 | 58.8 |
| C-DP 0.05 μm | −1.2 | 6.8 | 503.0 | 19.5 |

Figure 19:
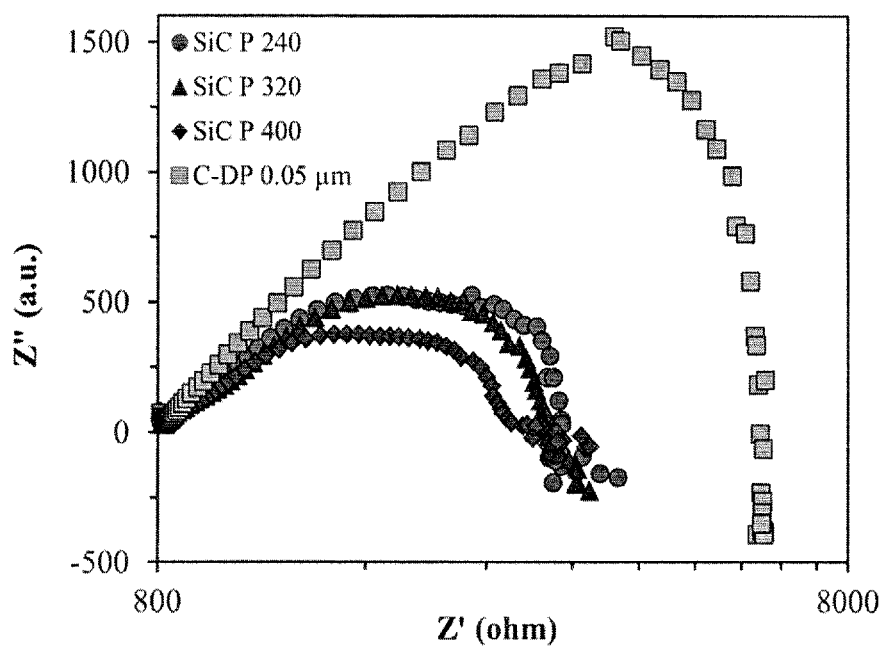
FIG. 19 shows the Nyquist plots of Mg1Zn1Ca alloys with different surface roughness tested in PBS at 37° C.
Figure 32:
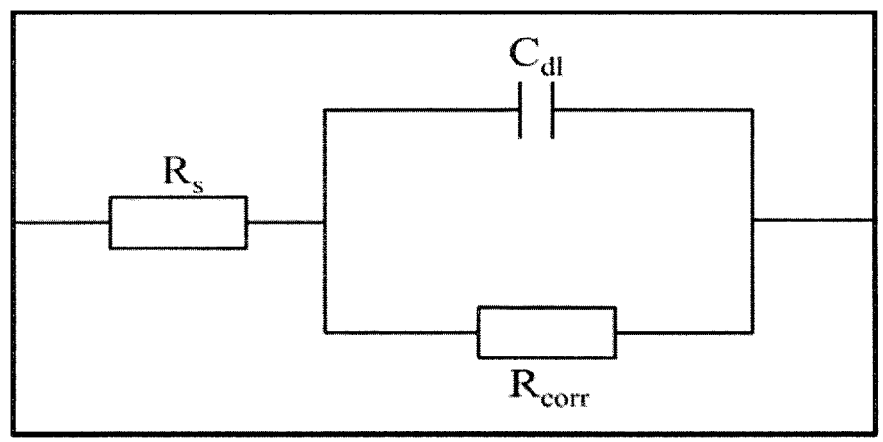
FIG. 32 shows an equivalent circuit of the corrosion cell, where $R_s$ is the electrolyte resistance, $R_{corr}$ is the charge transfer resistance, and $C_{dl}$ is the capacitance double layer.

The influence of surface roughness on the general corrosion resistance was investigated by EIS using a Gamry Echem Analyst software. FIG. 32 shows a Randles equivalent circuit, where $R_s$ is the electrolyte resistance, $R_{corr}$ is the charge transfer resistance, and $C_{dl}$ is the capacitance double layer. FIG. 19 shows the Nyquist plot where the highest impedance was observed for the smoothest samples. This could be ascribed to the formation of various oxides, which acted as an electric barrier. The capacitive arc provides an estimate of corrosion behavior of the material, in terms of the relative diameter of the capacitive arcs, which are directly proportional to the charge transfer resistance ($R_{ct}$). Thus, an increase in semicircle diameter corresponds to an increase in corrosion resistance. In this study, $I_{corr}$ increased as the degree of roughness increased. In the case of biodegradable alloys, an initial slow corrosion rate followed by uniform degradation is desirable.

Each sample displayed an inductive loop at low frequencies, which signifies that the alloys are susceptible to pitting corrosion. This occurs when Cl⁻ ions diffuse through a breach in the passivating layer, resulting in the formation of hydrolyzed metal chlorides. At anodic sites, $Mg^{++}$ ions are produced; Cl⁻ ions diffuse to such sites in order to establish electrical neutrality. Moreover, the increase in concentration of ions compresses the double-layer and increases the potential, whereas a low overvoltage cathode facilitates hydrogen evolution and alkalization of solution, causing a substantial corrosion rate.

The charge transfer resistances derived from the Nyquist plots are given in Table 11. Increase in charge transfer resistance with decreased roughness was observed, an effect that became more pronounced when surface roughness was 0.05 μm. This can be attributed to reduced corrosion rates and uniformity of surface oxides. The overall capacitance of the double layer ranged between 15 μF/cm² and 28 μF/cm².

TABLE 11

$R_{corr}$ and $C_{dl}$ values of Mg1Zn1Ca alloys in PBS at 37° C.

| Sample | $R_{corr}$ (Ω.cm²) | $C_{dl}$ (μF/cm²) |
|---|---|---|
| SiC P 240 | 511.8 | 17 |
| SiC P 320 | 495.3 | 23 |
| SiC P 400 | 405.2 | 28 |
| C-DP 0.05 μm | 1148.6 | 15 |

Figure 20A:
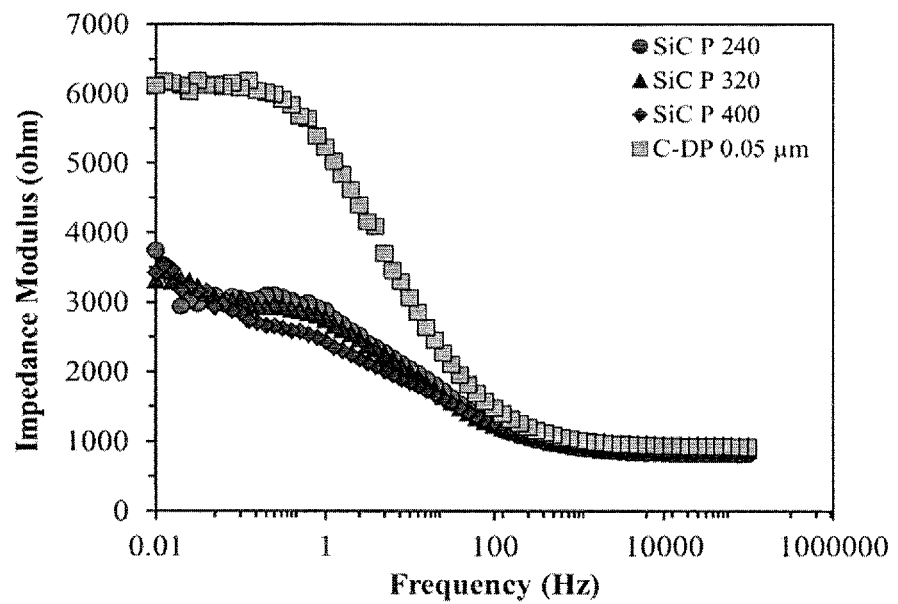
FIGS. 20A-20B are Bode plots of the impedance modulus (20A) and phase shift (20B) for Mg1Zn1Ca with different surface roughness in PBS at 37° C.
Figure 20B:
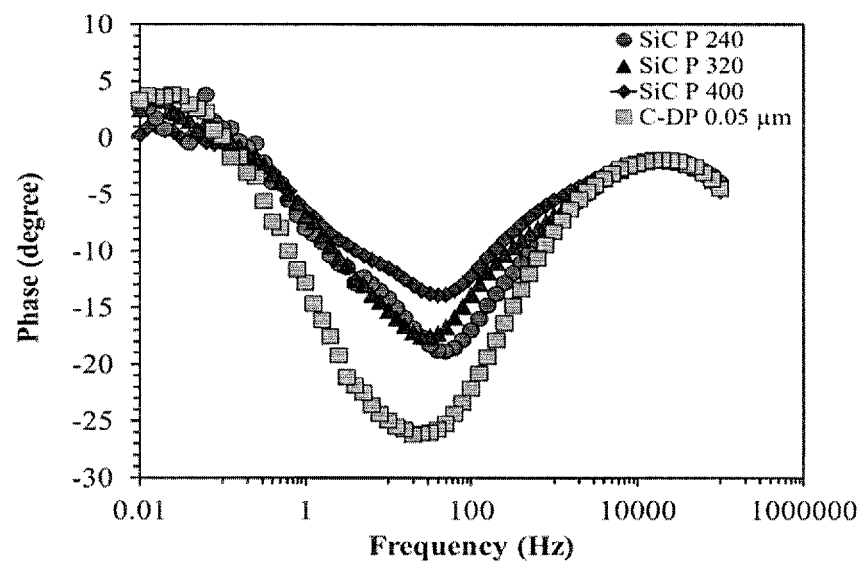

FIGS. 20A-20B show the Bode plot, where the impedance modulus and the phase shift are a function of frequency, provides information on the nature of the electrochemical processes. In the case of impedance modulus vs frequency (FIG. 20A), the high frequency domain represents the solution resistance ($R_s$) and the low frequency domain represents the system resistance, which mainly depends on the polarization resistance of the passivating film. Several oxides were produced, which resulted in a higher degree of phase shift at a frequency of approximately 80 Hz (FIG. 20B). This is most likely due to an increase in surface film capacitance with an increase in the adsorbed amount of ions on the electrode surface. The oxide layers produced on the surface of the alloys act as an electric barrier (resistance) that depends upon the charge transfer, and the symmetry of the Bode plot is an indication of the uniformity of the surface oxides. The loop is depressed and shifts a loop towards high frequency, which could be associated with the adsorption and desorption phenomena occurring on the surface of the samples. A layer of corrosion products and salt deposits formed from the solution instigated the slow degradation process. The formation of these oxides can impact long-term stability of an implant in biological environment and lead to slow degradation rates at the initial stage of implant's insertion. Increase in concentration of ions in solution decrease modulus value, while shifting phase to higher frequency. This could be due to an increase in surface film capacitance with an increase in adsorbed ions on the electrode surface.

The examples and embodiments described herein are for illustrative purposes only and various modifications or changes in light thereof will be apparent to persons skilled in the art and are included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

Example 7—Dual Surface Treatment (Anodization and Polymer Coating) Decreases Platelet Adhesion on MZC The amount of platelets adhered on A-P MZC (48 counts per $10^3$ μm$^2$) and was lower compared to that on mechanically polished MZC (80.5 counts per $10^3$ μm$^2$). To establish whether the magnitude of platelet adhesion per unit surface for each alloy was significantly different, ANOVA analysis was conducted. Platelet adhesion on A-P MZC was significantly different ($p<0.05$) from that on mechanically polished MZC.

FIG. 22 shows platelet adhesion on MP MZC, MP-A MZC sample and MP-A-P MZC with respect to surface chemistry, fractional polarity (FP), and contact angle (CA). The lowest concentration of platelet adhesion was observed on A-P MZC.

Figure 23:
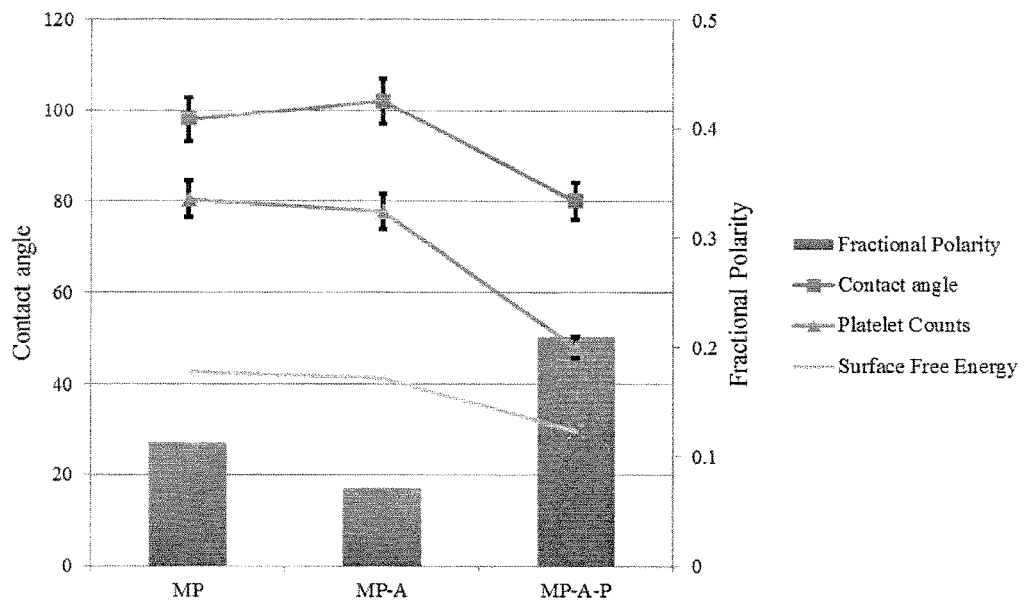
FIG. 23 shows platelet adhesion on MP MZC, MP-A MZC, and MP-A-P MZC samples with respect to surface chemistry, fractional polarity (FP), and contact angle (CA).
Figure 24:
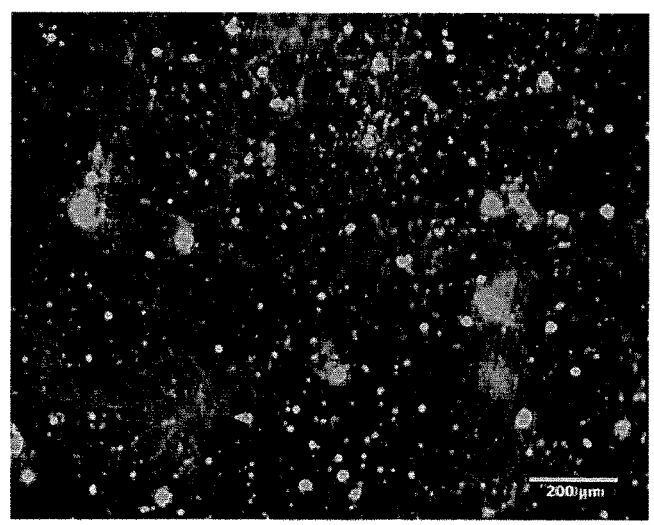
FIG. 24 is an optical micrograph of adhered platelets on MP MZC.
Figure 25:
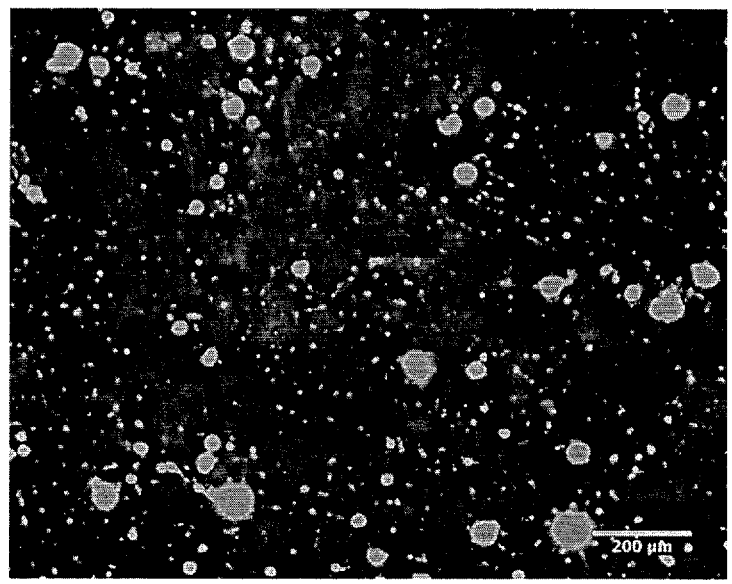
FIG. 25 is an optical micrograph of adhered platelets on (MP-A) MZC.
Figure 26:
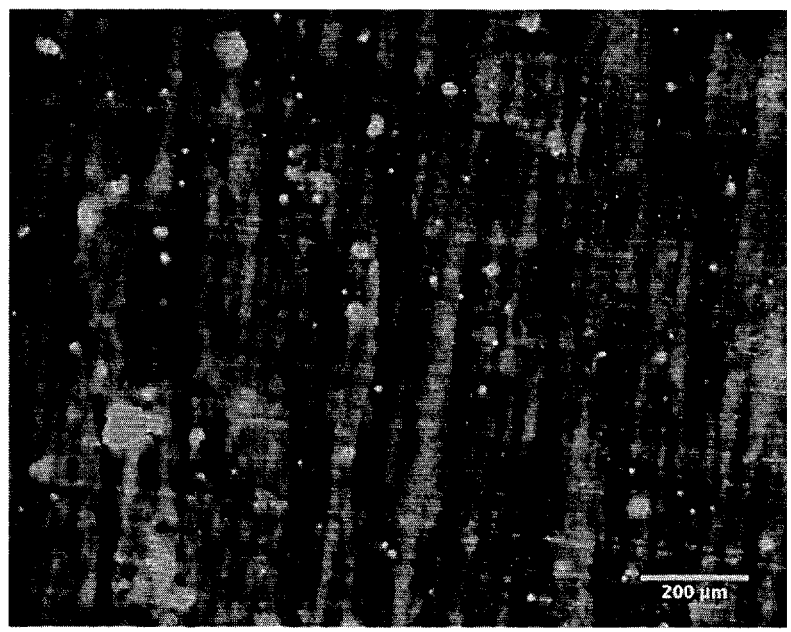
FIG. 26 is an optical micrograph of adhered platelets on (MP-A-P) MZC.

Platelet adhesion appears to be dependent on the hydrophobicity of the material's surface. As shown in FIG. 23, Polymer coating and anodization resulted in an increase in CA and a decrease in platelet adhesion. The fractional polarity (FP), which is derived from CA measurement, is inversely proportional to platelet adhesion. A-P MZC alloy had a lower surface free energy (SFE ~30 mJ/m$^2$) and higher fractional polarity (0.2) as compared with that of mechanically polished MZC of SFE (43 mJ/m$^2$) and fractional polarity (0.1).

Figure 27:
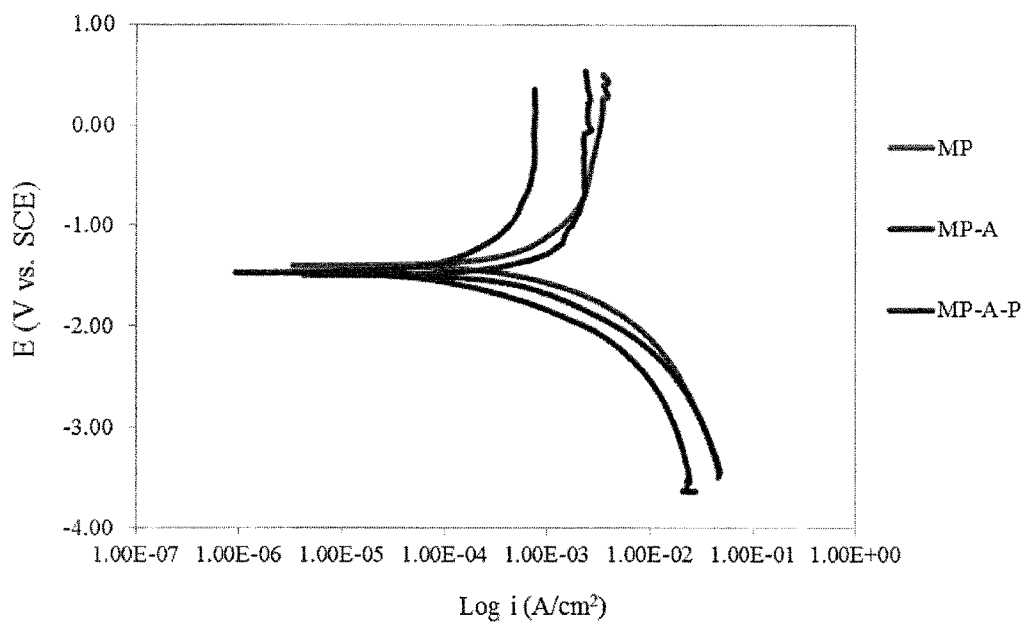
FIG. 27 shows potentiodynamic polarization curves for different surface-treated samples.
Figure 28:
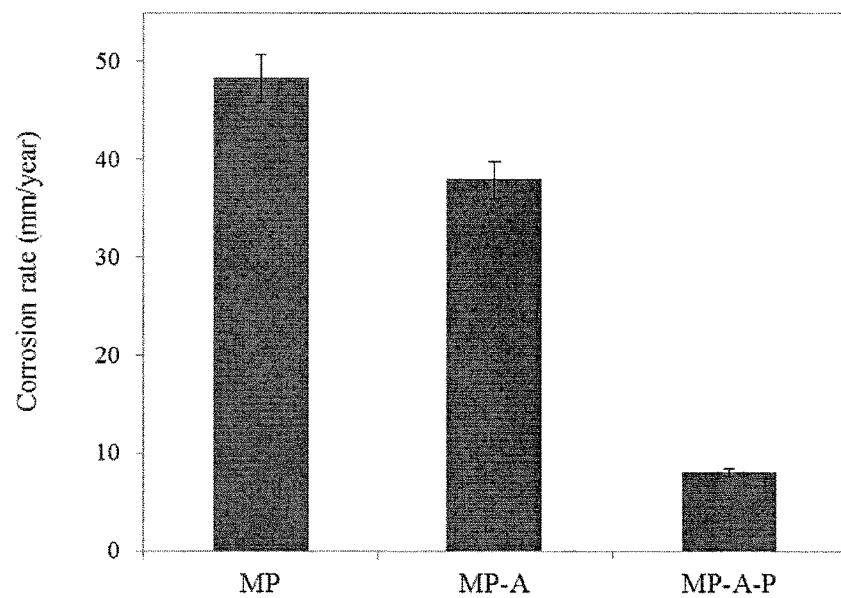
FIG. 28 shows the corrosion rates of different surface-treated samples.
Figure 29:
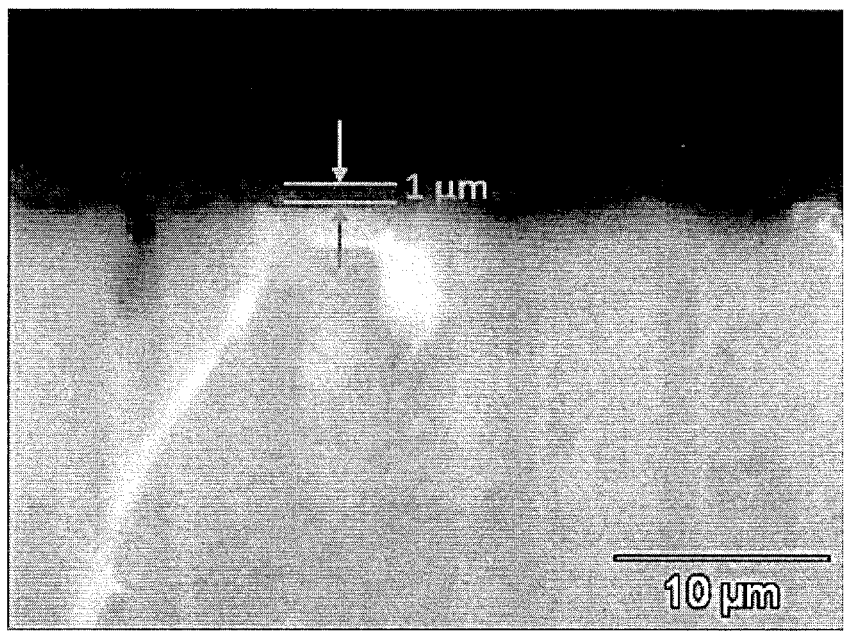
FIG. 29 is a cross-sectional view of an anodized sample.
Figure 30:
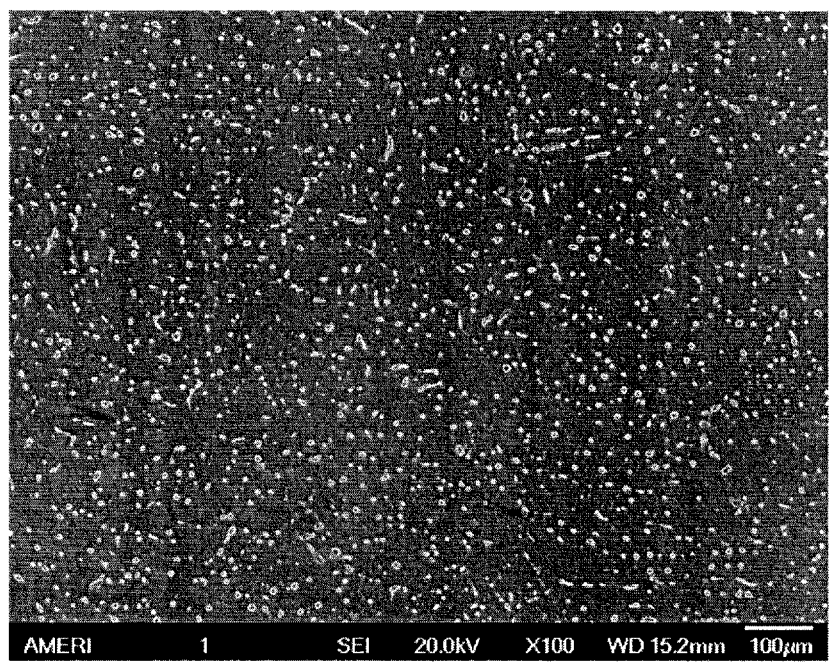
FIG. 30 is an SEM image of a heat-treated MZC sample.
Figure 31:
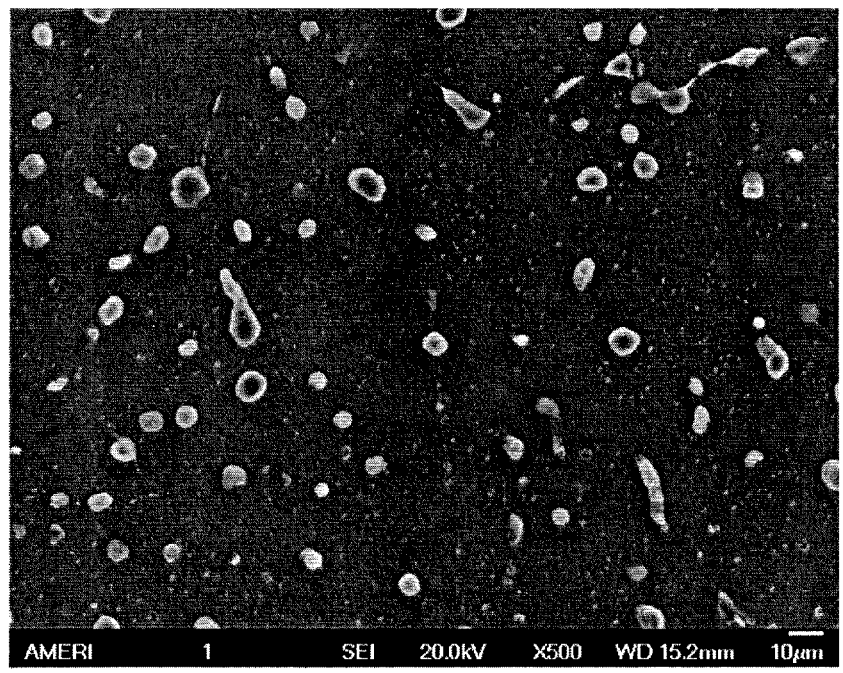
FIG. 31 is an SEM image of a heat-treated MZC sample.

Example 8—Dual Surface Treatment (Anodization and Polymer Coating) Improves Corrosion Resistance of MZC The corrosion resistance of the MZC was improved using anodization and polymer coating. The decrease in corrosion rate was attributed to the formation of a passive layer which restricted ionic transfer between the bulk of the material and the electrolyte. The polymer coating degraded uniformly and once fully degraded, the porous structure of anodized layer facilitated a gradual degradation of the bulk material. FIGS. 27 and 28 show that the least platelet adhesion and corrosion rate were observed on A-P MZC, implying antithrombogenic behavior.

All patents, patent applications, provisional applications, and publications referred to or cited herein (including those in the "References" section) are incorporated by reference in their entirety, including all figures and tables, to the extent they are not inconsistent with the explicit teachings of this specification.

REFERENCES

1. Zibiao L. Mg/Hydroxyapatite composites for potential bio-medical applications. Thesis submitted for the degree of M. Phil at the Brunel University, 2010.
2. Gill P, Munroe N. In-vitro corrosion studies of bioabsorbable alloys. Magnesium Technology, TMS, 2012.
3. Gill P, Munroe N, Dua R, Ramaswamy S. Corrosion and Biocompatibility Assessment of Magnesium Alloys. Journal of Biomaterials and Nanobiotechnology, 2012; 3:10-13.
4. Pound B G. Corrosion behavior of nitinol in blood serum and PBS containing amino acids. J Biomed Mater Res B Appl Biomater, 2010; 2:287-295.
5. Gill P, Munroe N, Pulletikurthi C, Pandya S, Haider W. Effect of manufacturing process on the biocompatibility and mechanical properties of Ti-30Ta Alloy. Journal of Materials Engineering and Performance. 2011; 20:4-7.
6. Schmidt M, Steinemann S G. XPS studies of amino acids adsorbed on titanium dioxide surfaces. J. Anal. Chem, 1991; 314:412-415.
7. Staiger M P, Pietak A M, Huadmai J, Dias G. Magnesium and its alloys as orthopedic biomaterials: A review. Biomaterials, 2006; 27:1728-1734.
8. Orazem M E, Tribollet B. Electrochemical Impedance Spectroscopy. John Wiley & Sons, Hoboken, N.J., 2008.
9. www.gamry.com/assets/Application-Notes/Basics-of-EIS.pdf, Accessed Apr. 6, 2012.
10. Zberg B, Uggowitzer P J, Löffler J F. MgZnCa glasses without clinically observable hydrogen evolution for biodegradable implants. Nature Materials. 2009; 8:887-891.
11. Erne P, Schier M., Resink T J. The Road to Bioabsorbable Stents: Reaching Clinical Reality? Cardiovasc. Inter. Rad., 2006; 29:11-16.
12. Heublein B, Rohde R, Kaese V, Niemeyer M, Hartung W, Haverich A. Biocorrosion of magnesium alloys: a new principle in cardiovascular implant technology? Heart, 2003; 89:651-656.
13. Erbel, R. et al. Temporary scaffolding of coronary arteries with bioabsorbable magnesium stents: a prospective, non-randomised multicentre trial. Lancet, 2007; 369: 1869-1875.
14. Peeters P, Bosiers M, Verbist J, Deloose K, Heublein B. Preliminary results after application of absorbable metal stents in patients with critical limb ischemia. J. Endovasc. Ther., 2005; 12:1-5.
15. Di Mario, C. et al. Drug-Eluting Bioabsorbable Magnesium Stent. J. Interv. Cardiol., 2004; 17:391-395.
16. Witte F. et al. In vitro and in vivo corrosion measurements of magnesium alloys. Biomaterials. 2006; 27:1013-1018.
17. Staiger M P, Pietak A M, Huadmai J, Dias G. Magnesium and its alloys as orthopaedic biomaterials: A review. Biomaterials, 2006; 27:1728-1734.
18. Witte F, Hort N, Vogt C, Cohen S, Kainer K U, Willumeit R, Feyerabend F. Degradable biomaterials based on magnesium corrosion. Current options in solid state and materials science. 2008; 12:63-72.
19. Song G, Song S. A possible biodegradable magnesium implant material. Advanced Engineering Materials, DOI: 10.1002/adem.200600252.
20. Langö T, Morland T, Brubakk A O. Diffusion coefficients and solubility coefficients for gases in biological fluids and tissues: a review. Undersea Hyperb Med, 1996; 23(4):247-72.
21. Song G. Control of biodegradation of biocompatable magnesium alloys. Corrosion Science, 2007; 49(4):1696-1701.
22. Song G L, Atrens A. Corrosion mechanisms of magnesium alloys. Advanced Engineering Materials, 1999; 1:11-33.

23. Wang Y, Lim C S, Lim C V, Yong M S, Teo E K, Moh L N. In vitro degradation behavior of M1A magnesium alloy in protein-containing simulated body fluid. Materials Science and Engineering C, 2011; 31:579-587.
24. Bolshakov A, Pharr G M. Influences of pileup on the measurement of mechanical properties by load and depth sensing indentation techniques. J. Mater. Res., 1998; 13:1049-1058.
25. Witte F, Feyerabend F, Maier P, Fischer J, Stormer M, Blawert C, Dietzel W, Hort N. Biodegradable magnesium-hydroxyapatite metal matrix composites. Biomaterials, 2007; 8:2163-2174.
26. Avedesian M M, Baker H. Magnesium and magnesium alloys. ASM International Handbook, 1999.
27. Ye X, Chen M, Yang M, Wei J, Liu D. In vitro corrosion resistance and cytocompatibility of nano-hydroxyapatite reinforced Mg—Zn—Zr composites. J Mater Sci: Mater Med. 2010; 21:1321-1328.
28. Kubásek J, Vojtěch D. Mechanical properties and corrosion behavior of biodegradable magnesium alloys. Metal, 2011; 18:1-6.
29. Li Z. Mg/Hydroxyapatite composites for potential biomedical applications, M. Phil, Brunel University, Brunel Center for Advanced Solidification Technology (BCAST), August 2010.
30. Ulery et al. (2011), Biomedical Applications of Biodegradable Polymers, *J Polym Sci B Polym Phys.;* 49(12): 832-864.
31. Sawyer et al. (1974), Electrochemical aspects of thrombogenesis—bioelectrochemistry old and new; *J. Electrochem. Sac.*: Reviews and News, 221C-234C.

We claim:

1. A method for treating a surface of an alloy, comprising treating the surface with all of the following: mechanical polishing, electrochemical treatment, and applying a polymer coating, wherein the alloy is Mg1Zn, Mg1Zn1Ca, Mg1Zn1Ca8Gd, Mg1Zn1Ca1HA, Mg1Zn1Ca3HA, Mg5Zn1Ca, Mg5Zn1Ca1HA, or Mg5Zn1Ca3HA, and wherein the electrochemical treatment comprises anodization.

2. The method of claim 1, wherein the mechanical polishing produces surface roughness of: 0.040 μm, 0.041 μm, 0.042 μm, 0.043 μm, 0.044 μm, 0.045 μm, 0.046 μm, 0.047 μm, 0.048 μm, 0.049 μm, 0.050 μm, 0.051 μm, 0.052 μm, 0.053 μm, 0.054 μm, 0.055 μm, 0.56 μm, 0.057 μm, 0.058 μm, 0.059 μm, 0.060 μm, 0.061 μm, 0.062 μm, 0.063 μm, 0.064 μm, 0.065 μm, 0.66 μm, 0.067 μm, 0.058 μm, 0.069 μm, or 0.070 μm.

3. The method of claim 1, wherein the polymer coating comprises a biodegradable polymer coating.

4. The method of claim 3, wherein the biodegradable polymer is poly(glycolic acid-co-caprolactone), poly(glycolic acid-co-trimethylene carbonate), poly(lactic-co-glycolic acid), or a combination thereof.

5. A device comprising an alloy, wherein a surface of the device is treated according to all of the following: mechanical polishing, an electrochemical treatment, and applying a polymer coating, wherein the alloy Mg1Zn, Mg1Zn1Ca, Mg1Zn1Ca8Gd, Mg1Zn1Ca1HA, Mg1Zn1Ca3HA, Mg5Zn1Ca, Mg5Zn1Ca1HA, or Mg5Zn1Ca3HA, and wherein the electrochemical treatment comprises anodization.

6. The device of claim 5, wherein:
a) the surface of the device has a roughness of: 0.040 μm, 0.041 μm, 0.042 μm, 0.043 μm, 0.044 μm, 0.045 μm, 0.046 μm, 0.047 μm, 0.048 μm, 0.049 μm, 0.050 μm, 0.051 μm, 0.052 μm, 0.053 μm, 0.054 μm, 0.055 μm, 0.56 μm, 0.057 μm, 0.058 μm, 0.059 μm, 0.060 μm, 0.061 μm, 0.062 μm, 0.063 μm, 0.064 μm, 0.065 μm, 0.66 μm, 0.067 μm, 0.058 μm, 0.069 μm, or 0.070 μm.

7. The device of claim 5, wherein the polymer coating comprises poly(glycolic acid-co-caprolactone), poly(glycolic acid-co-trimethylene carbonate), polylactic-co-glycolic acid), or a combination thereof.

8. The device of claim 7, wherein the device is an endovascular implant, a vascular implant, a drug-eluting stent, an orthopedic prosthesis, or a chip for biomarker labeling.

9. The device of claim 5, wherein the polymer coating comprises a biodegradable polymer coating.

10. A method of treating a subject by implanting the device of claim 8 into the subject.

11. A device comprising a biodegradable alloy, wherein a surface of the device is treated according to all of the following: mechanical polishing, electrochemical treatment, and applying a polymer coating;
wherein:
a) the biodegradable alloy is Mg1Zn, Mg1Zn1Ca, Mg1Zn1Ca8Gd, Mg1Zn1Ca1HA, Mg1Zn1Ca3HA, Mg5Zn1Ca, Mg5Zn1Ca1HA, or Mg5Zn1Ca3HA,
b) the surface of the device has a roughness from 0.040 μm to 0.060 μm,
c) the electrochemical treatment comprises anodization, and
d) the polymer coating comprises poly(glycolic acid-co-caprolactone), poly(glycolic acid-co-trimethylene carbonate), poly(lactic-co-glycolic acid), or a combination thereof.

12. The device of claim 11, wherein the device is an endovascular implant, a vascular implant, a drug-eluting stent, an orthopedic prosthesis, or a chip for biomarker labeling.

13. A method of treating a subject by implanting the device of claim 11 into the subject.

14. A method of treating a subject by implanting the device of claim 12 into the subject.

15. The device of claim 9, wherein the device is an endovascular implant, a vascular implant, a drug-eluting stent, an orthopedic prosthesis, or a chip for biomarker labeling.

16. A method of treating a subject by implanting the device of claim 15 into the subject.

* * * * *

UNITED STATES PATENT AND TRADEMARK OFFICE
CERTIFICATE OF CORRECTION

| | | |
|---|---|---|
| PATENT NO. | : 10,046,094 B1 | Page 1 of 1 |
| APPLICATION NO. | : 15/801574 | |
| DATED | : August 14, 2018 | |
| INVENTOR(S) | : Munroe et al. | |

It is certified that error appears in the above-identified patent and that said Letters Patent is hereby corrected as shown below:

On the Title Page

Item (72), should read:
Norman Munroe, Miami, FL (US);
Elnaz Mirtaheri, Miami, FL (US);
Sushma Armruthaluri, Herndon, VA (US);
Puneet Kamal Singh Gill, Anaheim, CA (US)

Signed and Sealed this
Eighth Day of June, 2021

Drew Hirshfeld
*Performing the Functions and Duties of the*
*Under Secretary of Commerce for Intellectual Property and*
*Director of the United States Patent and Trademark Office*